US012775014B2

(12) United States Patent
O'Mahony-Hartnett et al.

(10) Patent No.: US 12,775,014 B2
(45) Date of Patent: Oct. 27, 2026

(54) MULTIPARAMETER MATERIALS, METHODS AND SYSTEMS FOR ENHANCED BIOREACTOR MANUFACTURE

(71) Applicant: JANSSEN BIOTECH, INC., Horsham, PA (US)

(72) Inventors: Caitlin O'Mahony-Hartnett, County Cork (IE); Barry J. McCarthy, County Cork (IE); Christopher W. Rode, Raritan, NJ (US); Ronan Hayes, County Cork (IE); Fiona Madden, County Cork (IE); Jingjie Mo, Raritan, NJ (US); Francis C. Maslanka, Raritan, NJ (US); Kevin Clark, Raritan, NJ (US); Daniel A. Trout, Raritan, NJ (US); Pushpraj Rana, Raritan, NJ (US); Emmanouela Gratsia, Leiden (NL); Carl Rafferty, County Cork (IE); Karin M. Balss, Raritan, NJ (US); Olav Lyngberg, Raritan, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 448 days.

(21) Appl. No.: 18/283,694

(22) PCT Filed: Mar. 22, 2022

(86) PCT No.: PCT/US2022/021289

§ 371 (c)(1),
(2) Date: Sep. 22, 2023

(87) PCT Pub. No.: WO2022/204103

PCT Pub. Date: Sep. 29, 2022

(65) Prior Publication Data

US 2024/0168033 A1 May 23, 2024

Related U.S. Application Data

(60) Provisional application No. 63/165,040, filed on Mar. 23, 2021, provisional application No. 63/165,057,
(Continued)

(51) Int. Cl.
*G01N 33/68* (2006.01)
*C07K 1/107* (2006.01)
(Continued)

(52) U.S. Cl.
CPC ....... *G01N 33/6803* (2013.01); *C07K 1/1077* (2013.01); *C12M 41/32* (2013.01);
(Continued)

(58) Field of Classification Search
CPC .. C07K 1/1077; C07K 16/00; C07K 2317/41; C12M 41/32; C12P 21/005; G01N 21/65;
(Continued)

(56) References Cited

U.S. PATENT DOCUMENTS

2014/0349337 A1 11/2014 Dasari
2017/0355947 A9 12/2017 Berry
(Continued)

FOREIGN PATENT DOCUMENTS

WO WO-2008128225 A1 * 10/2008 ......... B01D 15/1864
WO 2016004322 1/2016

OTHER PUBLICATIONS

Berry et al., "Cross-scale predictive modeling of CHO cell culture growth and metabolites using Raman spectroscopy and multivariate analysis," Biotechnology Progress, vol. 31, No. 2 (2014), pp. 566-577.
(Continued)

*Primary Examiner* — Jennifer Wecker
(74) *Attorney, Agent, or Firm* — Riverside Law LLP

(57) ABSTRACT

Methods for determining glycation on a molecule and/or a glycan structure on a glycosylated molecule through the use
(Continued)

of a combination of spectroscopic analysis and chemometric modeling are described. In addition, methods and systems for producing a molecule with a desired level of glycation, including a non-glycated molecule, and/or a desired level of a glycan structure on a glycosylated molecule are described.

10 Claims, 14 Drawing Sheets

Related U.S. Application Data filed on Mar. 23, 2021, provisional application No. 63/165,055, filed on Mar. 23, 2021, provisional application No. 63/165,048, filed on Mar. 23, 2021.

(51) Int. Cl.
*C12M 1/34* (2006.01)
*G16B 40/10* (2019.01)
*G16C 20/20* (2019.01)
*G06F 16/25* (2019.01)

(52) U.S. Cl.
CPC ............. *G16B 40/10* (2019.02); *G16C 20/20* (2019.02); *G01N 2400/10* (2013.01); *G06F 16/258* (2019.01)

(58) Field of Classification Search
CPC ........... G01N 2400/10; G01N 2440/38; G01N 33/6803; G06F 16/258; G16B 15/20; G16B 40/10; G16C 20/10; G16C 20/20
See application file for complete search history.

(56) References Cited

U.S. PATENT DOCUMENTS

2018/0291329 A1 10/2018 Moretto
2021/0255173 A1* 8/2021 Kodama ................ A61K 40/11

OTHER PUBLICATIONS

Li et al., "Real-time monitoring of antibody glycosylation site occupancy by in situ Raman spectroscopy during bioreactor CHO cell cultures," Biotechnology Progress, vol. 34, No. 2 (Jan. 21, 2018), pp. 486-493.

Rowland-Jones et al., "Spectroscopy integration to miniature bioreactors and large scale production bioreactors—Increasing current capabilities and model transfer," Biotechnology Progress, vol. 37, No. e3074 (Sep. 19, 2020), 14 Pages.

Zavala-Ortiz et al., "Interest of locally weighted regression to overcome nonlinear effects during in situ NIR monitoring of CHO cell culture parameters and antibody glycosylation," Biotehnology Progress, vol. 36, No. e2924 (Oct. 14, 2019), 10 Pages.

Ast T et al., "Oxygen and mammalian cell culture: are we repeating the experiment of Dr. Ox?", Nat Metabol Nat Res, 2019, 1:858-860.

Brewster, V. L., et al., "Monitoring the Glycosylation Status of Proteins Using Raman Spectroscopy," Analytical Chemistry, vol. 83, No. 15 (2011), pp. 6074-6081.

Ghaderi D et al., "Production platforms for biotherapeutic glycoproteins. Occurrence, impact, and challenges of non-human sialylation", Biotechnol Gen Eng Rev, 2012, 28:147-176.

International Preliminary Report on Patentability for International Patent Application No. PCT/US2022/021289, Mailed Sep. 12, 2023, 8 Pages.

International Search Report for International Patent Application No. PCT/US2022/021289, Mailed Aug. 15, 2022, 3 Pages.

Kozlowski S et al., "Current and future issues in the manufacturing and development of monoclonal antibodies", Adv Drug Deliv Rev, 2006, 58(5-6):707-722.

Lewis AM et al., "Understanding and Controlling Sialylation in a CHO Fc-Fusion Process", PLoS One, 2016, 11(6): e0157111.

PDA, "Technical Report 56: Application of phase appropriate quality systems and cgmp to the development of therapeutic protein drug substance", Parenteral Drug Association: Bethesda, MD, 2012.

Quan C et al., "A study in glycation of a therapeutic recombinant humanized monoclonal antibody: Where it is, how it got there, and how it affects charge-based behavior", 2008, 373(2):179-191.

Templeton N et al., "Peak antibody production is associated with increased oxidative metabolism in an industrially relevant fed-batch CHO cell culture", Biotechnol Bioeng, 2013, 110:2013-2024.

Wei B et al., "Glycation of antibodies: modification, methods and potential effects on biological functions. mAbs", 2017, 9(4):586-594.

Xiao P et al., "Metabolic characterization of a CHO cell size increase phase in fed-batch cultures", Appl Microbiol Biotechnol, 2017, 101(22):8101-8113.

Yu LX et al., "Understanding pharmaceutical quality by design", AAPS J. 2014, 16(4):771-783.

* cited by examiner

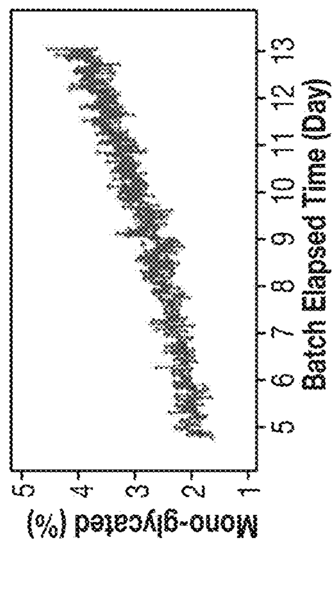
*FIG. 5A*
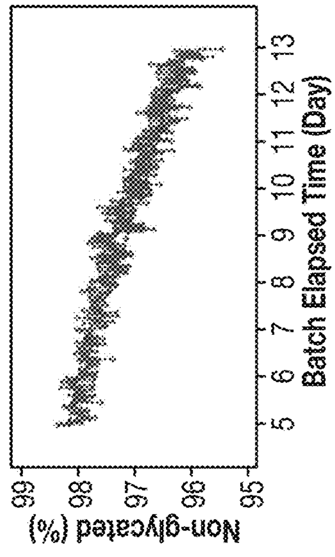
*FIG. 5B*
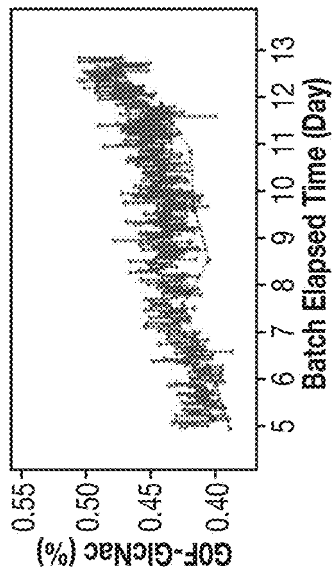
*FIG. 5C*
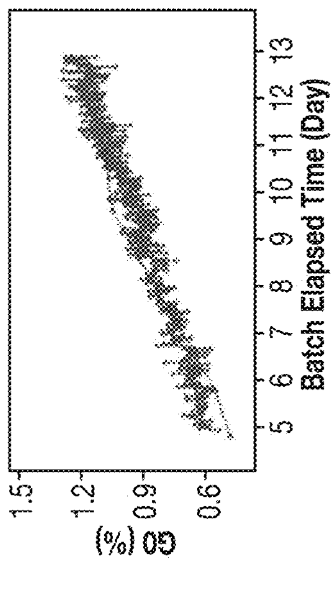
*FIG. 5D*
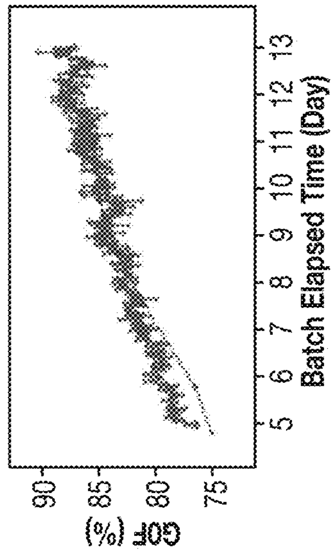
*FIG. 5E*
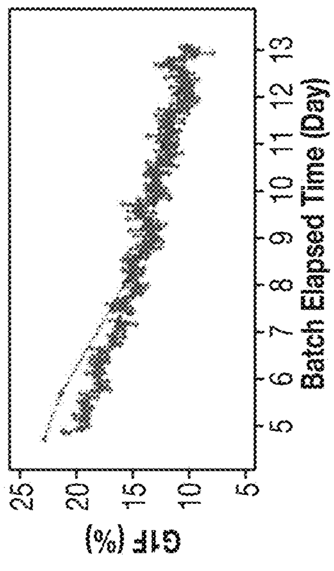
*FIG. 5F*
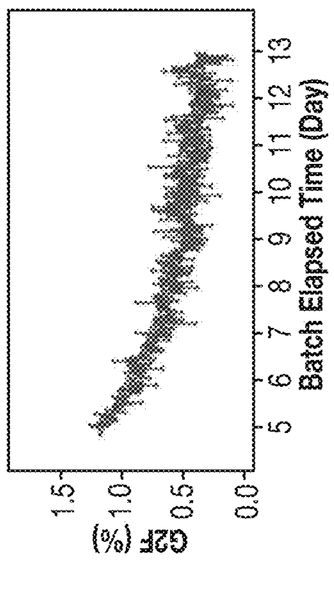
*FIG. 5G*
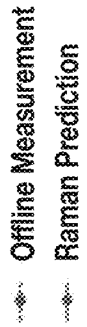

Legend — Flow 1 Model ··· Flow 3 Model

Legend -◆- Offline Measurement -◆- Raman Prediction

Legend ·+· Offline Measurement ·+· Raman Prediction

Legend — Batch A: Bolus Fed — Batch B: Glucose Control to 1g/L — Batch C: Glucose Control to 1g/L Legend Batch D: Bolus Fed Batch E: Glucose Control to 2g/L Batch F: Glucose Control to 2g/L

MULTIPARAMETER MATERIALS, METHODS AND SYSTEMS FOR ENHANCED BIOREACTOR MANUFACTURE

CROSS-REFERENCE TO RELATED APPLICATIONS

This application is a 371 national stage of PCT Application No. PCT/US2022/021289, filed on Mar. 22, 2022, which claims the benefit of U.S. Application No. 63/165,040, filed Mar. 23, 2021, U.S. Application No. 63/165,048, filed Mar. 23, 2021, U.S. Application No. 63/165,055, filed Mar. 23, 2021, and U.S. Application No. 63/165,057, filed Mar. 23, 2021, the disclosure of each of which is incorporated by reference herein in its entirety.

1. FIELD

The present disclosure relates, in part, to multiparameter materials, methods and systems for enhanced bioreactor manufacture. Specifically, the disclosure relates to methods and systems to control and monitor glycosylation of therapeutic proteins [e.g., recombinant proteins and/or monoclonal antibodies, (mAbs)] during the production process.

2. BACKGROUND

Glycation and glycosylation have been deemed a Critical Quality Attribute (CQA) to be considered in the production of therapeutic proteins. For example, glycation can potentially affect bioactivity and molecular stability of therapeutic proteins. Additionally, glycosylation of therapeutic proteins can influence the proteins' aggregation, solubility and stability both in vitro and in vivo. Therefore, detection and characterization of glycation and/or glycosylation are an important aspect of the production of therapeutic proteins.

3. SUMMARY

Against this background, the inventors of the present disclosure discovered methods and systems to control and monitor glycation and/or glycosylation of molecules (such as a therapeutic protein disclosed in Section 5.1) during the production process.

In one aspect, provided herein is a method for determining a glycan structure on a glycosylated molecule, the method comprising: obtaining, for each of a plurality of runs, levels for one or more glycan structures on the glycosylated molecule using a process analytical technology (PAT) tool, wherein the obtaining is within one or more first bioreactors having a first volume equal to or below a first threshold, the PAT tool obtaining spectral data; generating one or more regression models based on the obtained spectral data that correlate levels of the one or more glycan structures on the glycosylated molecule with the obtained spectral data; measuring the one or more glycan structures on the glycosylated molecule using the PAT tool, wherein the measuring is within one or more second bioreactors having a second volume equal to or above a second threshold to result in measured spectral data; and determining, by at least one computing device using the generated one or more regression models and based on the measured spectral data, levels of the one or more glycan structures on the glycosylated molecule within one or more second bioreactors.

In one embodiment, the method further includes refining the one or more regression models based on the combination of the obtained spectral data and the measured spectral data.

In one embodiment, the method further includes maintaining one or more operating parameters of the one or more second bioreactors based on the determined levels to produce a desired glycosylated molecule.

In one embodiment, the method further includes selectively modifying one or more operating parameters of the one or more second bioreactors based on the determined levels to produce a desired glycosylated molecule. In one embodiment, the one or more operating parameters comprise a pH level, a nutrient level, a culture media concentration, a frequency interval for culture media addition, or a combination thereof. In one embodiment, the nutrient level is selected from the group consisting of: a concentration of glucose, a concentration of lactate, a concentration of glutamine, and a concentration of ammonium ions. In one embodiment, the concentration of glucose is automatically modified based on the measured spectral data.

In one embodiment, the method further includes purifying the glycosylated molecule.

In one embodiment, the glycan structure is selected from the group consisting of: G0F-GlcNac, G0, G0F, G1F, and G2F, or a combination thereof.

In one embodiment, the obtaining is within two or more bioreactors having different volumes. In one embodiment, the first threshold is about 250 liters or less. In one embodiment, the first threshold is about 100 liters or less. In one embodiment, the first threshold is about 50 liters or less. In one embodiment, the first threshold is about 25 liters or less. In one embodiment, the first threshold is about 10 liters or less. In one embodiment, the first threshold is about 5 liters or less. In one embodiment, the first threshold is about 2 liters or less. In one embodiment, the first threshold is about 1 liter or less. In one embodiment, the second threshold is about 1,000 liters or more. In one embodiment, the second threshold is about 2,000 liters or more. In one embodiment, the second threshold is about 5,000 liters or more. In one embodiment, the second threshold is about 10,000 liters or more. In one embodiment, the second threshold is about 15,000 liters or more. In one embodiment, the second threshold is about 10,000 to about 25,000 liters. In one embodiment, the second threshold is about 15,000 liters. In one embodiment, the second threshold is at least 5× greater than the first threshold. In one embodiment, the second threshold is at least 10× greater than the first threshold. In one embodiment, the second threshold is at least 100× greater than the first threshold. In one embodiment, the second threshold is at least 500× greater than the first threshold. In one embodiment, the first volume is about 0.5 to about 250 liters. In one embodiment, the first volume is about 1 to about 50 liters. In one embodiment, the first volume is about 1 to about 25 liters. In one embodiment, the first volume is about 1 to about 10 liters. In one embodiment, the first volume is about 1 to about 5 liters. In one embodiment, the second volume is about 1,000 to about 25,000 liters. In one embodiment, the second volume is about 2,000 to about 25,000 liters. In one embodiment, the second volume is about 5,000 to about 25,000 liters. In one embodiment, the second volume is about 10,000 to about 25,000 liters. In one embodiment, the second volume is about 15,000 to about 25,000 liters.

In one embodiment, the PAT tool utilizes or otherwise comprises Raman spectroscopy.

In one embodiment, the one or more regression models comprise a partial least squares (PLS) model.

In one embodiment, the glycosylated molecule comprises a monoclonal antibody (mAb). In one embodiment, the glycosylated molecule comprises a non-mAb.

In one embodiment, the determining step is performed on-site. In one embodiment, the determining step is performed off-site.

In one embodiment, the determining step is performed in-line, at-line, on-line, off-line, or a combination thereof. In one embodiment, the determining step is performed on-line. In one embodiment, the determining step is performed at-line. In one embodiment, the determining step is performed off-line. In one embodiment, the determining step is performed in-line.

In one embodiment, the obtaining includes receiving data characterizing the spectral data from the PAT tool.

In one embodiment, the generating is executed by one or more computing devices.

In one aspect, provided herein is a method of producing a glycosylated molecule having a desired glycan structure, the method comprising: measuring one or more glycan structures using a process analytical technology (PAT) tool to result in spectral data, wherein the measuring is within a bioreactor having a volume of equal to or above 1,000 liters; determining, by at least one computing device using one or more regression models and based on the measured spectral data, a level of the one or more glycan structures within the bioreactor, wherein the one or more regression models are generated using trial runs from at least one bioreactor having a volume less than or equal to 50 liters and at least one bioreactor having a volume equal to or above 1,000 liters; and maintaining one or more operating parameters of the bioreactor when: the level of a desired glycan structure is above a pre-defined threshold, or the level of an undesired glycan structure is below a pre-defined threshold; or selectively modifying one or more operating parameters of the bioreactor when: the level of a desired glycan structures is below a pre-defined threshold, or the level of an undesired glycan structure is above a pre-defined threshold.

In one embodiment, the measuring is performed in-line, at-line, on-line, off-line, or a combination thereof. In one embodiment, the measuring is performed in-line. In one embodiment, the measuring is performed at-line. In one embodiment, the measuring is performed off-line. In one embodiment, the measuring is performed on-line.

In one embodiment, the measuring occurs more than once daily. In one embodiment, the measuring occurs about every 5 to 60 minutes. In one embodiment, the measuring occurs about every 10 to 30 minutes. In one embodiment, the measuring occurs about every 10 to 20 minutes. In one embodiment, the measuring occurs about every 12.5 minutes.

In one embodiment, the bioreactor volume is about 2,000 liters or more. In one embodiment, the bioreactor volume is about 5,000 liters or more. In one embodiment, the bioreactor volume is about 10,000 liters or more. In one embodiment, the bioreactor volume is about 15,000 liters or more. In one embodiment, the bioreactor volume is about 10,000 liters to about 25,000 liters. In one embodiment, the bioreactor volume is about 15,000 liters.

In one embodiment, the determining step is performed on-site. In one embodiment, the determining step is performed off-site.

In one embodiment, the desired glycan structure is selected from the group consisting of: G0F-GlcNac, G0, G0F, G1F, and G2F, or a combination thereof.

In one embodiment, the bioreactor is a batch reactor, a fed-batch reactor, a perfusion reactor, or a combination thereof.

In one embodiment, the one or more operating parameters include a pH level, a nutrient level, a culture media concentration, a frequency interval for culture media addition, or a combination thereof. In one embodiment, the nutrient level is selected from the group consisting of: a concentration of glucose, a concentration of lactate, a concentration of glutamine, and a concentration of ammonium ions. In one embodiment, the concentration of glucose is automatically modified based on the measured spectral data.

In one embodiment, the PAT tool includes Raman spectroscopy.

In one embodiment, the one or more regression models include a partial least squares (PLS) model.

In one aspect, provided herein is a system for producing one or more glycosylated molecules and the system includes a means for culturing a glycosylated molecule-producing cell line; means for measuring a level of one or more glycan structures, wherein the means generates spectral data; a means for generating one or more regression models based on the spectral data; and a means for measuring a level of one or more glycan structures in a glycosylated molecule-producing cell line.

In one embodiment, the glycosylated molecule-producing cell line is a mammalian cell line. In one embodiment, the mammalian cell line is a non-human cell line.

In one embodiment, the culturing includes batch, fed-batch, perfusion, of a combination thereof.

In one embodiment, culturing includes a volume of about 2,000 liters or more. In one embodiment, culturing includes a volume of about 5,000 liters or more. In one embodiment, the bioreactor volume is about 10,000 liters or more. In one embodiment, the bioreactor volume is about 15,000 liters or more. In one embodiment, culturing includes a volume of about 10,000 liters to about 25,000 liters. In one embodiment, culturing includes a volume of about 15,000 liters.

In one embodiment, measuring is performed in-line, at-line, on-line, off-line, or a combination thereof. In one embodiment, measuring is performed in-line. In one embodiment, measuring is performed on-line. In one embodiment, measuring is performed at-line. In one embodiment, measuring is performed off-line.

In one embodiment, measuring occurs more than once daily. In one embodiment, measuring occurs about every 5 to 60 minutes. In one embodiment, measuring occurs about every 10 to 30 minutes. In one embodiment, measuring occurs about every 10 to 20 minutes. In one embodiment, measuring occurs about every 12.5 minutes.

In one embodiment, the one or more glycan structures are selected from the group consisting of: G0F-GlcNac, G0, G0F, G1F, and G2F, or a combination thereof.

In one embodiment, the system further includes a means for selectively modifying one or more operating parameters to enhance production of a desired one or more glycan structures. In one embodiment, the one or more operating parameters include a pH level, a nutrient level, a culture media concentration, a frequency interval for culture media addition, or a combination thereof. In one embodiment, the nutrient level is selected from the group consisting of: a concentration of glucose, a concentration of lactate, a concentration of glutamine, and a concentration of ammonium ions. In one embodiment, the concentration of glucose is automatically modified based on the spectral data.

In one embodiment, the one or more glycosylated molecules include a monoclonal antibody (mAb). In one embodiment, the one or more glycosylated molecules include a non-mAb.

In one embodiment, the spectral data comprises Raman spectra.

In one embodiment, the one or more regression models comprise a partial least squares (PLS) model.

In one embodiment, the system further includes a means for isolating the one or more glycosylated molecules.

In one aspect, provided herein is a system for producing one or more glycosylated molecules, and the system includes: a bioreactor comprising a glycosylated molecule-producing cell line; a process analytical technology (PAT) tool that measures one or more glycan structures and generates spectral data; and a processor that correlates levels of one or more glycan structures with the spectral data using one or more regression models.

In one embodiment, the bioreactor is about 2,000 liters or more. In one embodiment, the bioreactor is about 5,000 liters or more. In one embodiment, the bioreactor volume is about 10,000 liters or more. In one embodiment, the bioreactor volume is about 15,000 liters or more. In one embodiment, the bioreactor is about 10,000 liters to about 25,000 liters. In one embodiment, the bioreactor is about 15,000 liters.

In one embodiment, the glycan structure is selected from the group consisting of: G0F-GlcNac, G0, G0F, G1F, and G2F, or a combination thereof.

In one embodiment, the glycosylated molecule-producing cell line is a mammalian cell line. In one embodiment, the mammalian cell line is a non-human cell line.

In one embodiment, the PAT tool utilizes or otherwise comprises Raman spectroscopy.

In one embodiment, the one or more regression models comprise a partial least squares (PLS) model.

Other aspects, features and advantages of the invention will be apparent from the following disclosure, including the detailed description of the invention and its preferred embodiments and the appended claims.

4. BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 5A-FIG. 5G illustrate Raman PLS model predictions (fluctuating blue line) vs. offline measurements (steady red line) for mono-glycation (FIG. 5A), non-glycation (FIG. 5B), G0F-GlcNac (FIG. 5C), G0 (FIG. 5D), G0F (FIG. 5E), G1F (FIG. 5F), and G2F (FIG. 5G) in manufacturing scale (2000 L) batch (CTSS) models using models supplemented with process data from a 2000 L scale batch run.

FIG. 15A-FIG. 1511 illustrate comparison of process trends for Cell Line 1 bolus fed and automated feedback control batches (FIG. 15A), VCD (FIG. 15B), Viability % (FIG. 15C), LDH (FIG. 15D), pH (FIG. 15E), O2 (FIG. 15F), Glucose Feed volume (FIG. 15G), Titer and (FIG. 15H) Glycation.

FIG. 16A-FIG. 1611 illustrate comparison of process trends for Cell Line 2 bolus fed and automated feedback control batches (FIG. 16A), VCD (FIG. 16B), Viability % (FIG. 16C), LDH (FIG. 16D), pH (FIG. 16E), O2 (FIG. 16F), Glucose Feed volume (FIG. 16G), Titer and (FIG. 16H) Glycation.

5. DETAILED DESCRIPTION

Figure 1A:
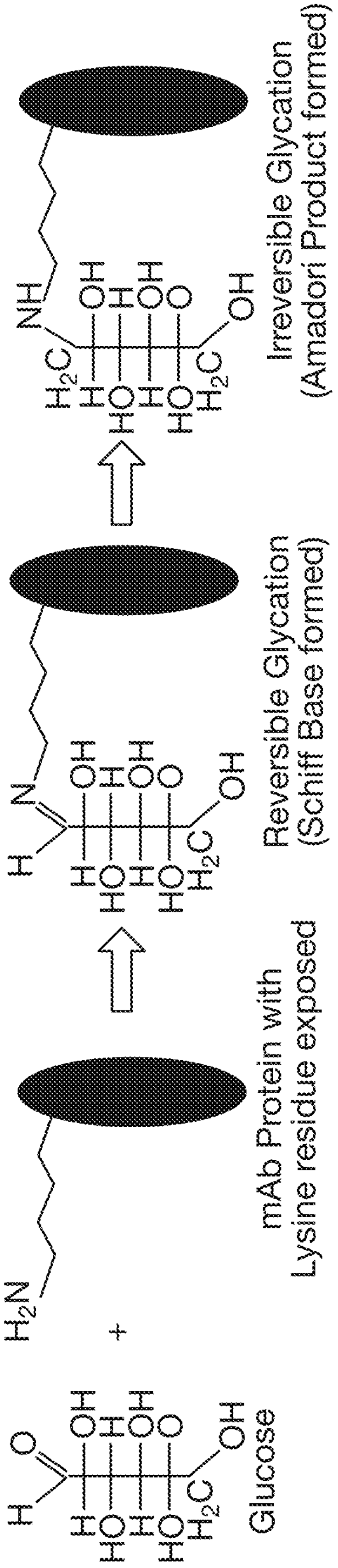
FIG. 1A and FIG. 1B illustrate the Maillard reaction for the glycation of mAbs (FIG. 1A), and common N-Glycan structures associated with N-linked glycosylation of therapeutic proteins such as mAbs (FIG. 1B).

Current methods for measuring glycation and glycosylation profiles include Boronate affinity chromatography, capillary isoelectric focusing colorimetric assays and liquid chromatography mass spectrometry (LC/MS). These methods, while capable of providing precise and accurate results are both time and resource consuming. Moreover, sampling often comes at the expense of product being removed from the bioreactor and a greater risk of contamination. Another drawback to the current methods is that they involve product quality testing once a batch has been completed.

Accordingly, there is an unmet need for methods and systems that can accurately monitor glycation and/or glycosylation throughout production of a therapeutic protein, which can enable a user with the ability to control glycation and/or glycosylation during the production process in real time.

The present disclosure is directed, in part, to methods and systems to control and monitor glycation and/or glycosylation of molecules (such as a therapeutic protein disclosed in Section 5.1) during the production process. For example, methods and systems are described herein that involve the partnering of a process analytical technology (PAT) tool and chemometric modelling to develop predictive models capable of monitoring glycation and glycosylation profiles, including individual glycoforms (microheterogeneity), with a specific focus on manufacturing scale processes. The present disclosure is also directed, in part, to the discovery that by including manufacturing scale data in the chemometric modelling, the predictive power and robustness of the model can be improved. Such methods and systems enable potential quality issues in the therapeutic protein production process to be identified before they impact the batch, and can also help reduce process variability, reduce supply costs due to yield improvements, carry out real time release of the product, reduce lead times and positively impact the technology transfer timelines of products due to a reduction in analytical method transfer and validation processes.

In some aspects, provided herein is a method for determining a glycan structure on a glycosylated molecule using PAT tool, such as Raman spectroscopy, and generating a regression model that can be used by a computing device to determine a level of one or more glycan structures on the therapeutic protein within a bioreactor. In other aspects, provided herein is a method for producing a glycosylated molecule having a desired glycan structure using a PAT tool that generates spectral data, and determining a level of one or more glycan structures on the therapeutic protein within a bioreactor by using one or more regression models. One or more operating parameters can then either be maintained or selectively modified based on the levels of the desired and/or undesired glycan structure. The present disclosure also provides a system for producing a one or more glycosylated molecules. The system can include a bioreactor comprising a cell line capable of producing the glycosylated molecule, a PAT tool that measures one or more glycan structures and generates spectral data, and a processor that correlates levels of one or more glycan structures with the spectral data using one or more regression models.

In some aspects, provided herein is a method for determining glycation on a molecule using a process analytical technology (PAT) tool, such as Raman spectroscopy, and generating a regression model that can be used by a computing device to determine glycation levels on a molecule within a bioreactor. In other aspects, provided herein is a method of producing a molecule with a desired level of glycation by measuring glycation on the molecule using a PAT tool that generates spectral data, and determining levels of glycation on the molecule by using one or more regression models. One or more operating parameters can then be either maintained or selectively modified based on the levels of glycation. The present disclosure also provides a system for producing a non-glycated molecule. The system can include a bioreactor comprising a cell line capable of producing the non-glycated molecule, a PAT tool that measures glycation and generates spectral data, and a processor that correlates levels of glycation with the spectral data using one or more regression models.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "molecule" generally refers to a protein, or fragment thereof. An exemplary molecule is a therapeutic protein (e.g., a recombinant protein or mAb) or fragment thereof.

As used herein, the term "bioreactor" generally refers to a device that supports a biologically active process, such as the culture of cells. Exemplary bioreactors include stainless steel stirred tank bioreactors, air-lift reactors, and disposable bioreactors.

As used herein, the term "spectral data" generally refers to the analytical output obtained using spectroscopy.

As used here, the term "threshold" generally refers to an amount that defines at least one limit, such as a lower limit or an upper limit, of a particular range or level. The threshold can be determined empirically, or it can be a pre-defined threshold that is set a priori.

As used herein, the term "selectively modifying" when used in reference to an operating parameter, generally refers to the purposeful adjustment of one or more conditions to facilitate optimal production of the desired product and/or decrease production of an undesired product.

As used herein, the term "automatically modified" generally means that an operating parameter is adjusted without the user needing to manually adjust the operating parameter.

As used herein, the term "on-site" generally means that the measuring or determining is performed at the same facility where production occurs.

As used herein, the term "off-site" generally means that the measuring or determining is performed at a facility different from where production occurs.

As used herein, the term "off-line" generally means that the measuring or determining is performed after the production process has complete, and collection of the sample is manual.

As used herein, the term "at-line" generally means the measuring or determining is performed within the production area, and collection of the sample is manual.

As used herein, the term "on-line" generally means that the measuring or determining is performed within the production area, and collection of the sample is automated.

As used herein, the term "in-line" generally means that the measuring or determining is performed in real time within the production area by a probe placed in the bioreactor and collection of a sample is not required.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., Molecular Cloning: A Laboratory Manual, Third Ed., Cold Spring Harbor Laboratory, New York (2001); Ausubel et al., Current Protocols in Molecular Biology, John Wiley and Sons, Baltimore, M D (1999); Glover, ed., DNA Cloning, Volumes I and II (1985); Freshney, ed., Animal Cell Culture: Immobilized Cells and Enzymes (IRL Press, 1986); Kallen et al, Plant Molecular Biology—A Laboratory Manual (Ed. by Melody S. Clark; Springer-Verlag, 1997); Immunochemical Methods in Cell and Molecular Biology (Academic Press, London); Scopes, Protein Purification: Principles and Practice (Springer Verlag, N.Y., 2d ed. 1987); National Research Council (US) Committee on Methods of Producing Monoclonal Antibodies. Monoclonal Antibody Production. Washington (DC): National Academies Press (US); 1999; and Clausen H, et al. Glycosylation Engineering. 2017. In: Varki A, Cummings R D, Esko J D, et al., editors. Essentials of Glycobiology. 3rd edition. Cold Spring Harbor (NY): Cold Spring Harbor Laboratory Press; 2015-2017; and National Research Council (US) Committee on Revealing Chemistry through Advanced Chemical Imaging. Visualizing Chemistry: The Progress and Promise of Advanced Chemical Imaging. Washington (DC): National Academies Press (US); 2006. 3, Imaging Techniques: State of the Art and Future Potential.

In an attempt to help the reader of the application, the description has been separated in various paragraphs or sections, or, is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. The application contemplates use of any of the applicable components in any combination, whether or not a particular combination is expressly described.

5.1. Therapeutic Proteins

The present disclosure is related, in part, to determining and/or measuring glycation and/or glycosylation of molecule. In certain embodiments, the molecule is a therapeutic protein. Non-limiting examples of therapeutic proteins include, for example, antibody-based drugs (e.g., polyclonal antibodies, or monoclonal antibodies (mAb)), Fc fusion proteins, anticoagulants, blood factors, bone morphogenetic proteins, engineered protein scaffolds, enzymes, growth factors, hormones, interferons, interleukins, recombinant proteins, and thrombolytics. Accordingly, in some embodiments, the molecule is a mAb. In some embodiments, the molecule is a recombinant protein. In some embodiments, the molecule is an Fc fusion protein. In some embodiments, the molecule is an anticoagulant. In some embodiments, the molecule is a blood factor. In some embodiments, the molecule is a bone morphogenetic protein. In some embodiments, the molecule is an engineered protein scaffold. In some embodiments, the molecule is an enzyme. In some embodiments, the molecule is a growth factor. In some embodiments, the molecule is a hormone. In some embodiments, the molecule is an interferon. In some embodiments, the molecule is an interleukin. In some embodiments, the molecule is a thrombolytic.

5.2. Glycation

The present disclosure is related, in part, to determining and/or measuring glycation of therapeutic proteins (such as a therapeutic protein disclosed in Section 5.1). Protein glycation is a non-enzymatic glycosylation on protein amine groups that generally occurs on the alpha amine terminal and epsilon amine group on the lysine side chain. Glycation involves a process by which reducing sugars, such as glucose, fructose and galactose, covalently binds to a protein in a non-enzymatic reaction. The reaction between the amino acid and reducing sugar was first described by Maillard in 1912. The susceptible amine group reversibly condenses with an aldehyde group of the reducing sugar, to form an unstable Schiff base intermediate, which can undergo a spontaneous multistep Amadori rearrangement to form a more stable, covalently bonded ketoamine. This reaction results in irreversible products causing biophysical and structural changes in proteins.

Glycation can potentially affect bioactivity and/or molecular stability of therapeutic proteins. For example, in the case of mAbs, which represent an exemplary therapeutic protein of the present disclosure, glycation can block the biologically functional site and/or cause degradation of the mAbs. The degradation may further lead to aggregation of the mAb. Consequently, glycation of therapeutic proteins represents a potential critical quality attribute (CQA) to the production process.

5.3. Glycosylation

The present disclosure is also related, in part, to determining, and/or measuring glycosylation, including specific glycan structures, of therapeutic proteins (such as a therapeutic protein disclosed in Section 5.1).

Glycosylation is a complex post translation modification that involves attachment of glycans to specific sites (e.g., N-linked and/or O-linked glycosylation) on the therapeutic protein. N-linked glycosylation of mAbs, for example, generally involves attachment of glycans at the Asn-X-Ser/Thr sequence of the Fc portion of mAb heavy chains, where X can be any amino acid except for proline (Ghaderi et al., 2012). For example, therapeutic proteins can include IgG1 molecules, which contain a single N-linked glycan at Asn297 in each of the two heavy chains. N-glycosylation can also occur in the variable region of each heavy chain (e.g., cetuximab). O-linked protein glycosylation generally involves a linkage between the monosaccharide N-Acetyl-galactosamine and the amino acids serine or threonine.

Figure 1B:
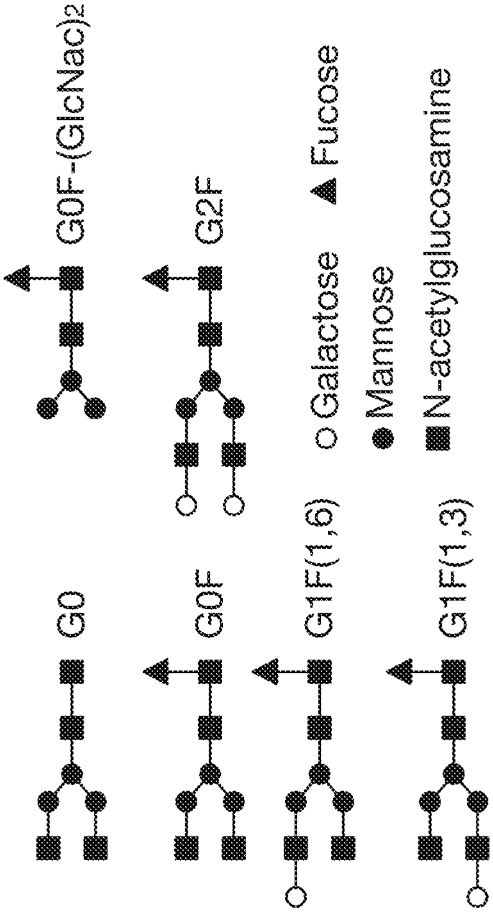
Figure 2:
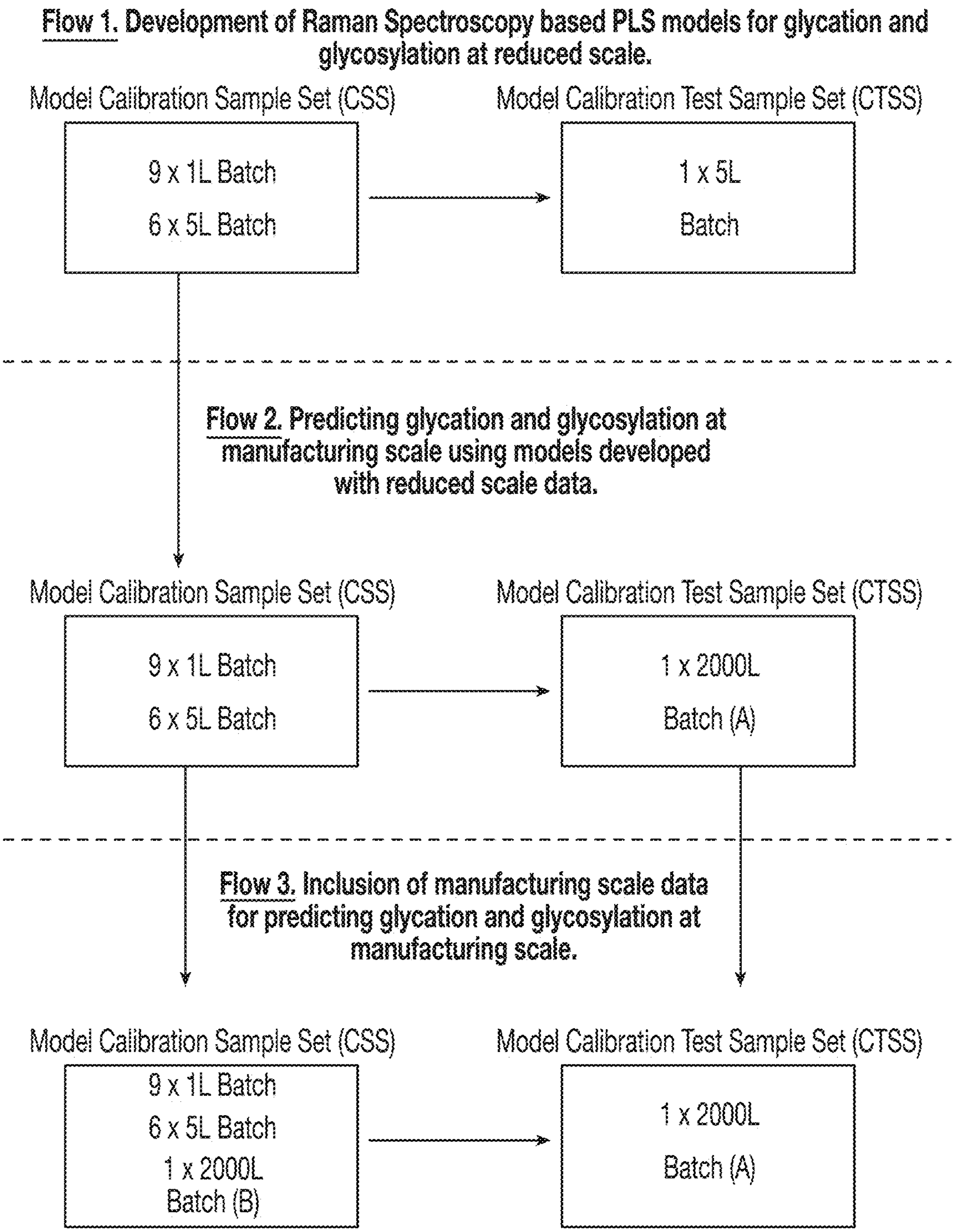
FIG. 2 illustrates a process flow for the development of and testing of Raman based PLS models.
Figure 3C:
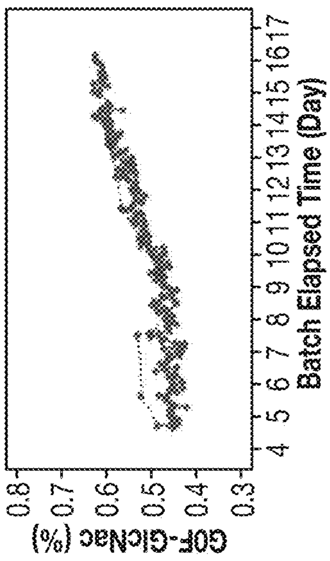
FIG. 3A-FIG. 3G illustrate Raman PLS model predictions (fluctuating blue line) vs. offline measurements (steady red line) for mono-glycation (FIG. 3A), non-glycation (FIG. 3B), G0F-GlcNac (FIG. 3C), G0 (FIG. 3D), G0F (FIG. 3E), G1F (FIG. 3F), and G2F (FIG. 3G) in reduced scale (5 L) batch (CTSS).
Figure 3F:
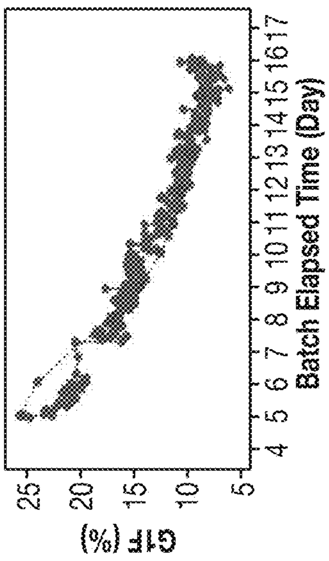
Figure 3B:
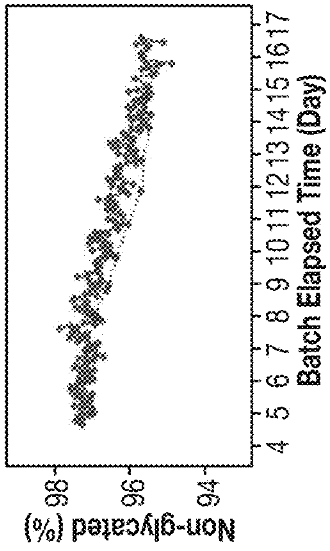
Figure 3E:
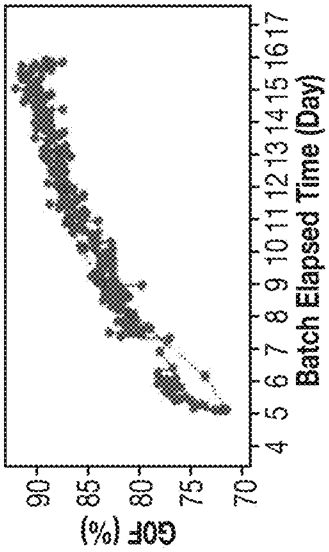
Figure 3A:
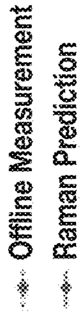
Figure 3A:
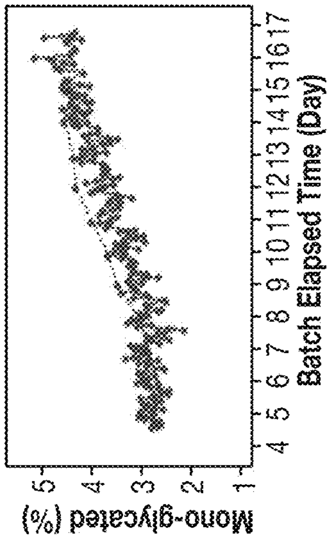
Figure 3D:
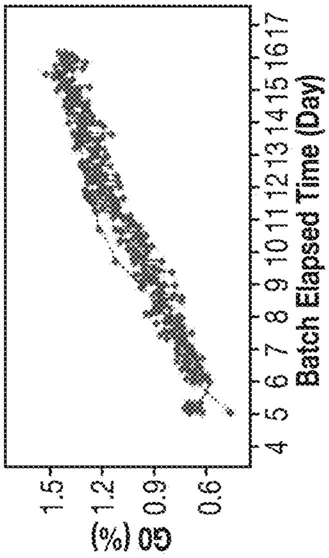
Figure 3G:
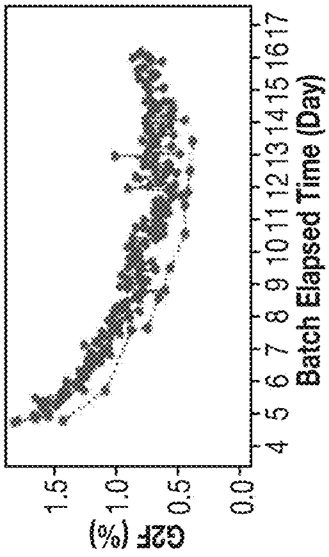

Depending on the arrangement of carbohydrate moieties covalently linked to specific regions of the therapeutic protein, classes of these carbohydrates (called "glycans") can be derived. For example, N-glycans include G0, G0F, G0F-GlcNac, G1F and G2F, which differ slightly in structure (see FIG. 1B). Variations in the structure of these glycans result in subtle changes in structure that can have a significant influence on protein activity, conformation, safety, and efficacy. As a result, glycosylation of therapeutic proteins has a pivotal role in their safety and efficacy, including immunogenicity, and appropriate glycosylation is one of the critical quality attributes (CQAs) that must be demonstrated to ensure the safety and potency of commercial therapeutic proteins, such as mAbs, before regulatory approval.

5.4. Process Analytical Technology (PAT)

Current methods for measuring glycation and glycosylation profiles include Boronate affinity chromatography, capillary isoelectric focusing colorimetric assays and liquid chromatography mass spectrometry (LC/MS). These methods, while capable of providing precise and accurate results are both time and resource consuming. Moreover, sampling using these methods often comes at the expense of product being removed from the bioreactor and a greater risk of contamination. Another drawback to the current methods is that they involve product quality testing once a batch has been completed.

As provided herein, the present disclosure relates, in part, to the measurement of glycation and/or glycosylation using Process Analytical Technology (PAT). PAT is advantageous because it can be used to control and monitor the production process before the batch has been completed. For example, PAT can allow samples to be measured in real time, such as by measuring in-line, or otherwise measured during the production process, such as by measuring at-line or on-line. Real time monitoring, for example, can increase process control, as it provides the opportunity to identify potential quality issues before they impact the batch, reduce process variability, reduce supply costs due to yield improvements, carry out real time release of the product, reduce lead times and positively impact the technology transfer timelines of products due to a reduction in analytical method transfer and validation processes. In contrast, complex and time-consuming methods that are reliant on the frequency at which off-line samples are measured only give a limited understanding of these CQAs, such as glycation and glycosylation, and are often only assessed after the bioreactor process has been completed. Therefore, by applying PAT during the production process, the quality of the product can be more carefully monitored and the final product produced will be a higher quality, as compared to production that relies on end-of-line testing to filter out the products that are outside their specifications.

5.4.1. PAT Tools

As provided herein, detection and/or measuring glycation and/or glycosylation can be carried out using PAT tools that involve spectroscopic techniques such as, for example, fluorescence spectroscopy, diffuse reflectance spectroscopy, infrared spectroscopy (e.g., near-infrared, or mid-infrared), terahertz spectroscopy, transmission and absorbance spectroscopy, Raman spectroscopy, including Surface Enhanced Raman Spectroscopy (SERS), Spatially Offset Raman spectroscopy (SORS), transmission Raman spectroscopy, and/or resonance Raman spectroscopy.

By way of example, Raman spectroscopy is a PAT tool capable of providing data that can be partnered with chemometric modelling (such as the chemometric modelling described in Section 5.4.2). It provides clear, sharp spectra, and can be optionally recorded within the bioreactor (e.g., in situ) using an in-situ probe during the production processes. Raman spectroscopy is a vibrational spectroscopic technique that uses laser technology to provide a chemical fingerprint of a substance.

Moreover, it has been used as a PAT tool to provide non-destructive real time measurement of a number of biotherapeutic process variables including metabolites, growth profiles, product levels, product quality attributes, nutrient feeds and more recently, culture pH. It should be understood, however, that other spectroscopic techniques can also be used with the methods and systems provided herein, and that Raman spectroscopy is merely an exemplary PAT tool.

Spectra obtained from any of the PAT tools described herein can be collected with a probe that is within the bioreactor (i.e., in situ), or by collecting a sample from the bioreactor and measuring the sample outside of the bioreactor. Spectra can also be coupled with multivariate analysis (MVA) to allow for monitoring of other operating parameters in addition to glycation and/or glycosylation such as, for example, metabolites, and/or cell concentration. For example, data on one or more operating parameters (e.g., pH, temperature, pressure, dissolved oxygen, optical density, oxygen uptake rate, etc.) can be combined with supporting information (raw material analysis, timing and duration of feeds, manual cell counts, metabolite levels, etc.) to generate large amounts of high dimensional data on the production process that can be handled by chemometric modeling methods such as the chemometric modeling described in Section 5.4.2). Spectra can also be collected pre and post glucose feeding.

Therefore, by combining spectroscopic analysis with chemometric modeling methods (such as the chemometric modeling described in Section 5.4.2), the real time monitoring of glycation and/or glycosylation, and optionally additional information on the production process, can be achieved. Therefore, spectroscopy, such as Raman spectroscopy, provides the ability to monitor bioprocesses during the production process rather than after the run is completed. As a result, spectroscopy can be used as a PAT tool for measuring glycation and/or glycosylation, with the option to implement the measurement results as a feedback loop that controls one or more operating parameters such as, for example, nutrient feeds, thereby leading to the desired amount of glycation and/or glycosylation, and optionally the specific glycan structure, on the therapeutic protein.

5.4.2. Chemometric Modeling

The spectroscopic methods provided herein can generate large amounts of high dimensional data. Generally, the data is handled by chemometric modeling methods using known techniques such as, for example, partial least square (PLS), classic least squares (CLS) or principle component analysis (PCA). The model is then built with the captured absorption spectra and reference levels obtained off-line, such as by liquid chromatography-mass spectrometry (LC-MS). The spectra can be subject to preprocessing methodologies, such as first and second or derivatives, extended multiplicative scattering correction, mean centering, and auto scaling, to name a few. The preprocessing methodologies can be used to help mitigate interferences such as cloudiness, or optical transmissibility, of the fluid, instrument drift, and contaminate build up on the lenses in contact with the fluid. The preprocessing methodologies also act as noise filters to enable models to focus on the real compositional changes in the fluid that may affect the resultant vapor pressure of the liquid. After that, the chemometric model is implemented to the PAT tool analyzer as the calibration curve to predict the glycation and/or glycosylation in real time.

Accordingly, in some embodiments, the one or more regression models is selected from the group consisting of partial least square (PLS), classic least squares (CLS) and principle component analysis (PCA). In some embodiments, the one or more regression models includes a partial least squares (PLS) model. In some embodiments, the one or more regression models includes a classic least squares (CLS) model. In some embodiments, the one or more regression models includes a principle component analysis (PCA).

5.4.3. Measurement Parameters.

As provided herein, glycation and/or glycosylation can be measured using a PAT tool, such as Raman spectroscopy, during the production process (e.g., at-line, on-line, and/or in-line), or after the production process is completed (e.g., off-line). Accordingly, in some embodiments, measuring is performed in-line, at-line, on-line, off-line, or a combination thereof. In some embodiments, the measuring is performed in-line. In some embodiments, the measuring is performed at-line. In some embodiments, the measuring is performed on-line. In some embodiments, the measuring is performed off-line.

Glycation and/or glycosylation can also be optionally measured on-site or off-site. In some embodiments, the measuring is performed on-site. In some embodiments, it is performed off-site.

The PAT tools disclosed herein that provide spectra, are capable of providing frequent measurement during the production process. For example, by using Raman spectroscopy, there is the potential to deliver a predicted value for a range of process variables normally confined to a single daily offline measurement as frequently as once every 15 minutes, when a single probe is in use, generating up to 360 times the amount of information versus a single daily offline measurement for a 16 day process.

Accordingly, in some embodiments measurement can occur more than once daily. If more frequent measurement is desired, measuring can occur about every 5 to 60 minutes, about every 10 to 30 minutes, about every 10 to 20 minutes, or about every 12.5 minutes. Generally, more frequent the measurements will be able to allow for more precise predictions of the glycation and/or glycosylation levels. In turn, this will allow the user ability to better control the molecule's glycation and/or glycosylation levels.

5.5. Production

As provided herein, the present disclosure relates, in part, to measuring glycation and/or glycosylation on therapeutic proteins (such as a therapeutic protein disclosed in Section 5.1) that are produced by culturing a biologically active organism (such as by using the cell culture methods described in Section 5.5.2) in bioreactors (such as the bioreactors describe in Section 5.5.1).

5.5.1. Bioreactors

As provided herein, the present disclosure relates, in part, to measuring glycation and/or glycosylation on therapeutic proteins (such as a therapeutic protein disclosed in Section 5.1) that are grown in bioreactors. Various types of bioreactors can be used for production of the therapeutic protein. For example, the bioreactor can be a stainless steel stirred tank bioreactor (STR), an air-lift reactor, a disposable bioreactor, or a combination thereof (e.g., a disposable bioreactor combined with the STR).

The bioreactor can have any suitable volume that allows for the cultivation and propagation of biological cells capable of producing therapeutic proteins (such as a therapeutic protein disclosed in Section 5.1). For example, the volume of the bioreactor can be about 0.5 liters (L) to about 25,000 L. In some embodiments, the volume of the bioreactor can be less than or equal to about 250 L. In some embodiments, the volume of the bioreactor can be about 0.5 liters (L) to about 250 L. In some embodiments, the volume of the bioreactor can be less than or equal to about 50 L. In some embodiments, the volume of the bioreactor can be about 1 L to about 50 L. In some embodiments, the volume of the bioreactor can be less than or equal to about 25 L. In some embodiments, the volume of the bioreactor can be about 1 L to about 25 L. In some embodiments, the volume of the bioreactor can be less than or equal to about 10 L. In some embodiments, the volume of the bioreactor can be less than or equal to about 5 L. In some embodiments, the volume of the bioreactor can be less than or equal to about 1 L. In some embodiments, the volume of the bioreactor can be about 1 L. In some embodiments, the volume of the bioreactor can be about 2 L. In some embodiments, the volume of the bioreactor can be less than or equal to about 5 L. In some embodiments, the volume of the bioreactor can be less than or equal to about 10 L. In some embodiments, the volume of the bioreactor can be less than or equal to about 25 L. In some embodiments, the volume of the bioreactor can be less than or equal to about 50 L. In some embodiments, the volume of the bioreactor can be less than or equal to about 100 L. In some embodiments, the volume of the bioreactor can be less than or equal to about 250 L. In some embodiments, the volume of the bioreactor can equal to or above 1,000 L. In some embodiments, the volume of the bioreactor can be about 1,000 L to about 25,000 L. In some embodiments, the volume of the bioreactor can be about 10,000 L to about 25,000 L. In some embodiments, the volume of the bioreactor can be about 1,000 L. In some embodiments, the volume of the bioreactor can be about 2,000 L. In some embodiments, the volume of the bioreactor can be less than or equal to about 5,000 L. In some embodiments, the volume of the bioreactor can be less than or equal to about 10,000 L. In some embodiments, the volume of the bioreactor can be less than or equal to about 15,000 L. In some embodiments, the volume of the bioreactor can be less than or equal to about 25,000 L.

As provided herein, in certain aspects of the present disclosure, chemometric models can be first generated using data obtained from reduced scale bioreactors (e.g., less than 250 L), and the robustness and predictive power of the chemometric models can be increased by refining the model using data obtained from the manufacturing scale bioreactor (e.g., greater than or equal to 2,000 L, and preferably between 10,000 L to 25,000 L) for use in predicting glycation and/or glycosylation at manufacturing scale. Accordingly, in some embodiments, the methods and systems described herein involve two or more bioreactors having different volumes.

The addition of data obtained from the manufacturing scale bioreactor improves the model's ability to predict. This may be due to the changes in the bioreactor culture that occur in the manufacturing scale bioreactor, but not in the reduced scale process. For example, culture mixing time, $CO_2$ removal and oxygen transfer rates can differ with the manufacturing scale. By way of example, a reduced oxygen transfer in the manufacturing scale process has the potential to influence the glycation and, in particular, the glycosylation profiles of the mAb products in a way that would not be seen at the reduced scale. A reduced oxygen transfer leads to potential presence of 'dead zones' areas in the bioreactor where no oxygen is present for brief periods (Ast et al., 2019). This leads to an increased oxidative stress on the host cells in the bioreactor. Oxidative stress has been reported to have an effect on the glycosylation of mAbs as this stress reduces acetyl-CoA formation which in turn leads to a decreased N-acetylglucosamine (GlcNac) (Lewis et al., 2016), a key amide which forms part of the backbone structure of glycosylation targets described here, apart from G0F-GlcNac. Therefore, by incorporating data obtained from the manufacturing scale process, these variations can be accounted for in the model, and help improve the model's predictability.

Thus, in some embodiments, the chemometric model involves data generated from one or more first bioreactors, as well as data generated from one or more second bioreactors. In some embodiments, each of the one or more first bioreactors has a maximum threshold volume of less than or equal to about 250 L. In some embodiments, each of the one or more first bioreactors has a maximum threshold volume of less than or equal to about 100 L. In some embodiments, each of the one or more first bioreactors has a maximum threshold volume of less than or equal to about 50 L. In some embodiments, each of the one or more first bioreactors has a maximum threshold volume of less than or equal to about 25 L. In some embodiments, each of the one or more first bioreactors has a maximum threshold volume of less than or equal to about 10 L. In some embodiments, each of the one or more first bioreactors has a maximum threshold volume of less than or equal to about 5 L. In some embodiments, each of the one or more first bioreactors has a maximum threshold volume of less than or equal to about 2 L. In some embodiments, each of the one or more first bioreactors has a maximum threshold volume of less than or equal to about 1 L In some embodiments, each of the one or more first bioreactors has a volume of less than or equal to about 250 L. In some embodiments, each of the one or more first bioreactors has a volume of less than or equal to about 100 L. In some embodiments, each of the one or more first bioreactors has a volume of less than or equal to about 50 L. In some embodiments, each of the one or more first bioreactors has a volume of less than or equal to about 25 L. In some embodiments, each of the one or more first bioreactors has a volume of less than or equal to about 10 L. In some embodiments, each of the one or more first bioreactors has a volume of less than or equal to about 5 L. In some embodiments, each of the one or more first bioreactors has a volume of less than or equal to about 2 L. In some embodiments, each of the one or more first bioreactors has a volume of less than or equal to about 1 L. In some embodiments, the volume of each of the one or more first bioreactors can be about 0.5 liters (L) to about 250 L. In some embodiments, the volume of each of the bioreactors can be about 1 L to about 50 L. In some embodiments, the volume of each of the one or more first bioreactors can be about 1 L to about 25 L. In some embodiments, the volume of each of the one or more first bioreactors can be about 1 L to about 10 L. In some embodiments, the volume of each of the one or more first bioreactors can be about 1 L to about 5 L.

In some embodiments, each of the one or more second bioreactors has a minimum threshold volume of greater than or equal to about 1,000 L. In some embodiments, each of the one or more second bioreactors has a minimum threshold volume of greater than or equal to about 2,000 L. In some embodiments, each of the one or more second bioreactors has a minimum threshold volume of greater than or equal to about 5,000 L. In some embodiments, each of the one or more second bioreactors has a minimum threshold volume of greater than or equal to about 10,000 L. In some embodiments, each of the one or more second bioreactors has a minimum threshold volume of greater than or equal to about 15,000 L. In some embodiments, each of the one or more second bioreactors has a minimum threshold volume of greater than or equal to about 20,000 L. In some embodiments, each of the one or more second bioreactors has a minimum threshold volume of greater than or equal to about 25,000 L. In some embodiments, each of the one or more second bioreactors has a minimum threshold volume of about 2,000 L to about 25,000 L. In some embodiments, each of the one or more second bioreactors has a minimum threshold volume of about 5,000 L to about 25,000 L. In some embodiments, each of the one or more second bioreactors has a minimum threshold volume of about 10,000 L to about 25,000 L. In a preferred embodiment, each of the one or more bioreactors has a minimum threshold volume equal to the volume of the bioreactor used for manufacturing the therapeutic protein. In some embodiments, each of the one or more second bioreactors has a volume of greater than or equal to about 1,000 L. In some embodiments, each of the one or more second bioreactors has a volume of greater than or equal to about 2,000 L. In some embodiments, each of the one or more second bioreactors has a volume of greater than or equal to about 5,000 L. In some embodiments, each of the one or more second bioreactors has a volume of greater than or equal to about 10,000 L. In some embodiments, each of the one or more second bioreactors has a volume of greater than or equal to about 15,000 L. In some embodiments, each of the one or more second bioreactors has a volume of greater than or equal to about 20,000 L. In some embodiments, each of the one or more second bioreactors has a volume of greater than or equal to about 25,000 L. In some embodiments, each of the one or more second bioreactors has a volume of about 1,000 L to about 25,000 L. In some embodiments, each of the one or more second bioreactors has a volume of about 2,000 L to about 25,000 L. In some embodiments, each of the second bioreactors has a volume of about 5,000 L to about 25,000 L. In some embodiments, each of the second bioreactors has a volume of about 10,000 L to about 25,000 L. In some embodiments, each of the one or more second bioreactors has a volume of about 15,000 L to about 25,000 L. In a preferred embodiment, each of the one or more bioreactors has a volume equal to the volume of the bioreactor used for manufacturing the therapeutic protein.

In some embodiments, each of the one or more second bioreactors has a minimum threshold volume that is at least five times (5×) greater than the maximum threshold volume of each of the one of more first bioreactors. In some embodiments, each of the one or more second bioreactors has a minimum threshold volume that is at least 10× greater than the maximum threshold volume of each of the one or more first bioreactors. In some embodiments, each of the one or more second bioreactors has a minimum threshold volume that is at least 25× greater than the maximum threshold volume of each of the one or more first bioreactors. In some embodiments, each of the one or more second bioreactors has a minimum threshold volume that is at least 50× greater than the maximum threshold volume of each of the one or more first bioreactors. In some embodiments, each of the one or more second bioreactors has a minimum threshold volume that is at least 100× greater than the maximum threshold volume of each of the one or more first bioreactors. In some embodiments, each of the one or more second bioreactors has a minimum threshold volume that is at least 250× greater than the maximum threshold volume of each of the one or more first bioreactors. In some embodiments, each of the one or more second bioreactors has a minimum threshold volume that is at least 500× greater than the maximum threshold volume of each of the one or more first bioreactors. In some embodiments, each of the one or more second bioreactors has a minimum threshold volume that is at least 1,000× greater than the maximum threshold volume of each of the one or more first bioreactors. In some embodiments, each of the one or more second bioreactors has a volume that is at least five times (5×) greater than the volume of each of the one or more first bioreactors. In some embodiments, each of the one or more second bioreactors has a volume that is at least 10× greater than the volume of each of the one or more first bioreactors. In some embodiments, each of the one or more second bioreactors has a volume that is at least 25× greater than the volume of each of the one or more first bioreactors. In some embodiments, each of the one or more second bioreactors has a volume that is at least 50× greater than the volume of each of the one or more first bioreactors. In some embodiments, each of the one or more second bioreactors has a volume that is at least 100× greater than the volume of each of the one or more first bioreactors. In some embodiments, each of the one or more second bioreactors has a volume that is at least 250× greater than the volume of each of the one or more first bioreactors. In some embodiments, each of the one or more second bioreactors has a volume that is at least 500× greater than the volume of each of the one or more first bioreactors. In some embodiments, each of the one or more second bioreactors has a volume that is at least 1,000× greater than the volume of each of the one or more first bioreactors.

5.5.2. Cell Culture Methods

The production of the therapeutic proteins (such as a therapeutic protein disclosed in Section 5.1) of the present disclosure can be performed with any suitable biologically active host-cell type known in the art to be capable of producing therapeutic proteins. For example, mammalian cells and non-mammalian cells can be used as platforms for the production of therapeutic proteins. Non-limiting examples of mammalian host cell lines for production of therapeutic proteins include the Chinese hamster ovary (CHO), mouse myeloma derived NS0 and Sp2/0 cells, human embryonic kidney cells (HEK293), and human embryonic retinoblast-derived PER.C6 cells. Non-limiting examples of non-mammalian hosts include, for example, *Pichia pastoris, Arabidopsis thaliana, Nicotiana benthamiana, Aspergillus niger*, and *Escherichia coli*. Accordingly, in some embodiments, the therapeutic protein-producing cell line is a mammalian cell line. In some embodiments, the mammalian cell line is a non-human cell line.

Different host systems may express varying glycosylation enzymes and transporters, contributing to the specificity and heterogeneity in glycosylation profiles of the therapeutic protein. Similarly, different host systems may have different effects on the glycation levels of the therapeutic protein. Therefore, it is possible to engineer or specifically select a host-cell line that can generate the desired therapeutic protein with, for example, a specific glycan structure and/or level of glycation.

Cultivation and propagation of the biologically active cells can be performed using various methods known in the art, such as batch process, fed-batch process, continuous culture, or a combination thereof (e.g., a hybrid between fed batch and perfusion).

In the batch method, all nutrients are supplied at the beginning of the cultivation, without adding any more in the subsequent bioprocess. During the entire bioprocess, no additional nutrients are added, but control elements such as gases, acids and bases may optionally be added. The bioprocess then lasts until the nutrients are consumed.

The fed-batch method adds nutrients into the bioreactor as a large bolus at set time points or once they are depleted. Generally, the same medium used in the initial culture is also used for feeding, but in a more concentrated version. The feeding solution composition can be designed to supply the cells based on their metabolic state at different culture phases such as by, for example, analyzing and identifying the spent medium nutrients that are being consumed at greater rates. In addition, the medium used in the fed-batch method can even be modified to accommodate the needs of the cell culture or promote production of the therapeutic protein, such as to promote cell growth or to stimulate production of the therapeutic protein. For example, in some embodiments, the medium can be modified to reduce or eliminate glycation of the therapeutic protein.

In continuous culture, nutrients are continuously added to the bioreactor and, generally, an equivalent amount of converted nutrient solution is simultaneously taken out of the system. The three most common types of continuous culture are chemostat, turbidostat, and perfusion. The perfusion method circulates medium through a growing culture, allowing simultaneous removal of waste, supply of nutrients, and harvesting of product.

As provided herein, in some embodiments, the feeding is automated. In certain aspects, the feeding is automated and automation controls one or more operating parameters (such as the operating parameters described in Section 5.5.3).

5.5.3. Operating Parameters

Glycation of therapeutic proteins can occur during the production process, where a reducing sugar, such as glucose, is used as an energy source for a biologically active organism, such as a cell culture that produces the therapeutic protein. The level of glycation can be affected by the amount of sugar that is added to the cell culture during the mammalian cell culture process. In addition, other factors, such as pH level, nutrient levels, time (e.g., the frequency interval for culture media addition), temperature, and ionic strength, can affect the kinetics and extent of glycation. Moreover, the specific types of sugars used in the cell culture media, such as hexose sugars, for example, and the specific reactivity of the accessible amino groups can affect the protein glycation.

Many process parameters can shape the glycosylation of therapeutic proteins such as, for example, dissolved oxygen (DO) levels, culture temperatures of bioreactor, host-cell type, and nutrient or supplement availability.

Accordingly, in some embodiments, one or more operating parameters of the bioreactor is maintained or selectively modified based on the determined glycation and/or glycosylation levels to produce a therapeutic protein with an acceptable amount of glycation and/or glycosylation. In some embodiments, the operating parameter includes a temperature, pH level, a dissolved oxygen (DO) level, a nutrient level, a culture media concentration, a frequency interval for culture media addition, or a combination thereof.

In some embodiments, the operating parameter includes a temperature. For example, if the therapeutic protein has a desirable amount of glycation and/or glycosylation, the temperature of the bioreactor can be maintained at or around the temperature in the bioreactor at the time of measuring the glycation and/or glycosylation level. Alternatively, if the therapeutic protein has an undesirable amount of glycation and/or glycosylation, the temperature of the bioreactor can be adjusted for a portion or the entirely of the production process to achieve the desired amount of glycation and/or glycosylation. In some embodiments, the temperature is a physiological temperature. In some embodiments, the temperature is maintained or adjusted to a temperature of about 25° C. to 42° C. In some embodiments, the temperature is maintained or adjusted to a temperature of about 35° C. to 39° C. In some embodiments, the temperature is maintained or adjusted to a temperature of about 35.5° C. to 37.5° C. In some embodiments, the temperature is maintained or adjusted to a temperature of about 35° C. In some embodiments, the temperature is maintained or adjusted to a temperature of about 35.5° C. In some embodiments, the temperature is maintained or adjusted to a temperature of about 36° C. In some embodiments, the temperature is maintained or adjusted to a temperature of about 36.5° C. In some embodiments, the temperature is maintained or adjusted to a temperature of about 37° C. In some embodiments, the temperature is maintained or adjusted to a temperature of about 37.5° C. In certain embodiments, the temperature in the bioreactor is a non-physiological temperature. In some embodiments, the temperature is maintained or adjusted to a temperature of less than 25° C. In some embodiments, temperature is maintained or adjusted to a temperature of about 4° C. to about 25° C. In some embodiments, temperature is maintained or adjusted to a temperature of about 4° C. to about 10° C. In some embodiments, the temperature is maintained or adjusted to a temperature of about 4° C. In some embodiments, the temperature is maintained or adjusted to a temperature of about 5° C. In some embodiments, the temperature is maintained or adjusted to a temperature of about 6° C. In some embodiments, the temperature is maintained or adjusted to a temperature of about 7° C. In some embodiments, the temperature is maintained or adjusted to a temperature of about 8° C. In some embodiments, the temperature is maintained or adjusted to a temperature of about 9° C. In some embodiments, the temperature is maintained or adjusted to a temperature of about 10° C.

In some embodiments, the operating parameter includes a pH level that is either maintained or modified, depending on the measured level of glycation and/or glycosylation on the therapeutic protein. For example, if the therapeutic protein has a desirable amount of glycation and/or glycosylation, the pH in the bioreactor can be maintained at or around the pH level in the bioreactor at the time of measuring the glycation and/or glycosylation level. High pH (≥7.0) can be beneficial for initial cell growth phase. However, high pH, high lactate and high osmolality cascade often causes delayed cell growth and accelerated cell death. Accordingly, the pH level may also need to be adjusted during the production process depending on what phase of growth the biologically active cells are in. For example, pH can be maintained or adjusted using addition(s) of carbon dioxide and/or sodium carbonate.

In some embodiments, the pH is a physiological pH. In some embodiments, the pH is between pH 4.0 to pH 9.0. In some embodiments, the pH is between pH 5.0 to pH 8.0. In some embodiments, the pH is between pH 6.0 to pH 7.0. In some embodiments, the pH is between pH 4.0 to pH 6.0. In some embodiments, the pH is between pH 5.0 to pH 7. In some embodiments, the pH is between pH 6.0 to pH 8.0. In some embodiments, the pH is maintained or adjusted to about pH 4.0. In some embodiments, the pH is maintained or adjusted to about pH 4.5. In some embodiments, the pH is maintained or adjusted to about pH 5.0. In some embodiments, the pH is maintained or adjusted to about pH 5.5. In some embodiments, the pH is maintained or adjusted to about pH 6.0. In some embodiments, the pH is maintained or adjusted to about pH 6.5. In some embodiments, the pH is maintained or adjusted to about pH 6.6. In some embodiments, the pH is maintained or adjusted to about pH 6.7. In some embodiments, the pH is maintained or adjusted to about pH 6.8. In some embodiments, the pH is maintained or adjusted to about pH 6.9. In some embodiments, the pH is maintained or adjusted to about pH 7.0. In some embodiments, the pH is maintained or adjusted to about pH 7.1. In some embodiments, the pH is maintained or adjusted to about pH 7.2. In some embodiments, the pH is maintained or adjusted to about pH 7.3. In some embodiments, the pH is maintained or adjusted to about pH 7.4. In some embodiments, the pH is maintained or adjusted to about pH 7.5. In some embodiments, the pH is maintained or adjusted to about pH 7.6. In some embodiments, the pH is maintained or adjusted to about pH 7.7. In some embodiments, the pH is maintained or adjusted to about pH 7.8. In some embodiments, the pH is maintained or adjusted to about pH 7.9. In some embodiments, the pH is maintained or adjusted to about pH 8.0.

In some embodiments, the operating parameter includes a culture media glucose concentration. For example, if the therapeutic protein has a desirable level of glycation and/or glycosylation, the culture media glucose concentration that is added to the bioreactor, such as by fed-batch culture or perfusion culture, or hybrid fed-batch and perfusion glucose concentration can be maintained at or around the target concentration in use at the time of measuring the glycation and/or glycosylation level.

In some embodiments, the operating parameter includes the frequency internal for culture media glucose addition. For example, if the therapeutic protein has a desirable level of glycation and/or glycosylation, the frequency interval for culture media glucose addition to the bioreactor, such as in a fed-batch culture or perfusion culture, or hybrid fed-batch and perfusion glucose concentration can be maintained at or around the frequency at the time of measuring the glycation and/or glycosylation level. In some embodiments, the frequency is maintained or adjusted such that the culture media addition is continuous. In some embodiments, the frequency is maintained or adjusted such that the culture media addition is at split intervals, for example, six hours. In some embodiments, the frequency is maintained or adjusted such that the culture media addition is at split intervals, for example, twelve hours. In some embodiments, the frequency is maintained or adjusted such that the culture media addition is daily bolus, for example, twenty-four hours. In some embodiments, the frequency is maintained or adjusted such that the culture media addition is longer than every twenty-four hours.

In some embodiments, the operating parameter includes a nutrient level. In some embodiments, the nutrient level is selected from the group consisting of: a concentration of glucose, a concentration of lactate, a concentration of glutamine, and a concentration of ammonium ions. In some embodiments, the operating parameter includes a concentration of glucose. In some embodiments, the operating parameter includes a concentration of lactate. In some embodiments, the operating parameter includes a concentration of glutamine. In some embodiments, the operating parameter includes a concentration of ammonium ions.

In certain embodiments, the glucose concentration is maintained or adjusted to about 0.5 g/L to about 40 g/L, depending on the cell density. In certain embodiments, the glucose concentration is maintained or adjusted to about 0.5 g/L to about 30 g/L. In certain embodiments, the glucose concentration is maintained or adjusted to about 0.5 g/L to about 20 g/L. In certain embodiments, the glucose concentration is maintained or adjusted to about 0.5 g/L to about 10 g/L. In certain embodiments, the glucose concentration is maintained or adjusted to about 0.5 g/L to about 5 g/L. In certain embodiments, the glucose concentration is maintained or adjusted to about 5 g/L to about 40 g/L. In certain embodiments, the glucose concentration is maintained or adjusted to about 10 g/L to about 40 g/L. In certain embodiments, the glucose concentration is maintained or adjusted to about 20 g/L to about 40 g/L. In certain embodiments, the glucose concentration is maintained or adjusted to about 30 g/L to about 40 g/L. In certain embodiments, the glucose concentration is maintained or adjusted to about 35 g/L to about 40 g/L. In certain embodiments, the glucose concentration is maintained or adjusted to about 10 g/L to about 30 g/L. In certain embodiments, the glucose concentration is maintained or adjusted to about 10 g/L to about 20 g/L. In certain embodiments, the glucose concentration is maintained or adjusted to about 5 g/L to about 10 g/L. In certain embodiments, the glucose concentration is maintained or adjusted to about 10 g/L to about 15 g/L. In certain embodiments, the glucose concentration is maintained or adjusted to about 15 g/L to about 20 g/L. In certain embodiments, the glucose concentration is maintained or adjusted to about 20 g/L to about 25 g/L. In certain embodiments, the glucose concentration is maintained or adjusted to about 25 g/L to about 30 g/L. In certain embodiments, the glucose concentration is maintained or adjusted to about 30 g/L to about 35 g/L.

By way of example, a therapeutic protein that has an acceptable level of glycation can have the concentration of a reducing sugar, such as glucose, maintained. Alternatively, as further example, a therapeutic protein that has an undesirable amount of glycation can have a nutrient level, such as the concentration of a reducing sugar, decreased, and/or the frequency of culture media addition can be decreased. It would be within the skillset of a person skilled in the art to understand how much the operating parameters should be adjusted, if at all. Moreover, other alternative operating parameters can be adjusted according to the glycation levels, and it should be understood that the examples described above are intended to be merely exemplary.

Similarly, a therapeutic protein that has an acceptable level of a specific glycan structure can have one or more operating parameters maintained. Alternatively, a therapeutic protein that has an undesirable level of a specific glycan structure can have one or more operating parameters adjusted to control the specific glycan structure.

In certain aspects, the one or more operating parameter automatically modified based on the measure spectral data. For example, glycation and/or glycosylation can be measured using a PAT tool, such as a PAT tool described in Section 5.4.1, and the one or more operating parameters can be automatically maintained in the bioreactor if the level of a desired glycan structure is above a pre-defined threshold, or the level of an undesired glycan structure is below a pre-defined threshold. Alternatively, the one or more operating parameters can be automatically modified in the bioreactor if the level of a desired glycan structures is below a pre-defined threshold, or the level of an undesired glycan structure is above a pre-defined threshold.

The threshold of an acceptable level of glycation on the therapeutic protein will generally be determined empirically. In some embodiments, the pre-defined threshold of glycation will be less than 50% of the therapeutic protein in the bioreactor. In some embodiments, the pre-defined threshold of glycation will be less than 40%. In some embodiments, the pre-defined threshold of glycation will be less than 30%. In some embodiments, the pre-defined threshold of glycation will be less than 25%. In some embodiments, the pre-defined threshold of glycation will be less than 20%. In some embodiments, the pre-defined threshold of glycation will be less than 15%. In some embodiments, the pre-defined threshold of glycation will be less than 10%.

Accordingly, in some embodiments, at least 90% of the therapeutic protein in the bioreactor will be non-glycated. In some embodiments, at least 85% of the therapeutic protein in the bioreactor will be non-glycated. In some embodiments, at least 80% of the therapeutic protein in the bioreactor will be non-glycated. In some embodiments, at least 75% of the therapeutic protein in the bioreactor will be non-glycated. In some embodiments, at least 70% of the therapeutic protein in the bioreactor will be non-glycated. In some embodiments, at least 60% of the therapeutic protein in the bioreactor will be non-glycated. In some embodiments, at least 50% of the therapeutic protein in the bioreactor will be non-glycated.

The threshold for the level of glycation on the therapeutic protein will also generally be determined empirically. For example, some level of variability in the batch to batch glycoform content in a production setting are to be expected, and generally the threshold will be an acceptable limit that does not produce too much variability in the glycoform content. Accordingly, in some embodiments the pre-defined threshold of an undesirable glycan structure will be less than 50% of the therapeutic protein in the bioreactor. In some embodiments, the pre-defined threshold of an undesirable glycan structure will be less than 40%. In some embodiments, the pre-defined threshold of an undesirable glycan structure will be less than 30%. In some embodiments, the pre-defined threshold of an undesirable glycan structure will be less than 25%. In some embodiments, the pre-defined threshold of an undesirable glycan structure will be less than 20%. In some embodiments, the pre-defined threshold of an undesirable glycan structure will be less than 15%. In some embodiments, the pre-defined threshold of an undesirable glycan structure will be less than 10%.

5.5.4. Purification.

Generally, the therapeutic proteins (such as a therapeutic protein disclosed in Section 5.1) are secreted from the cells grown during the production process. After the production process is completed, the therapeutic protein can be separated from the cells and purified using any technique known in the art suitable for protein purification, including purification according to FDA standards. Preferably, the purification will remove process impurities, such as host cell proteins, nucleic acids, and/or lipids.

The purification process can involve one or more steps. For example, purification of the therapeutic protein can involve primary recovery, purification, and/or polishing steps. Generally, the primary recovery step consists of centrifugation and/or depth filtration in order to remove the cells and cell debris from the culture broth and clarification of the cell culture supernatant that contains the therapeutic protein product. Additional techniques known in the art can be additionally included to improve in the primary recovery process. For example, the use of flocculants such as simple acids, divalent cations, polycationic polymers, caprylic acid and stimulus-responsible polymers can enhance cell culture clarification and reduce the levels of cells, cellular debris, DNA, host cell proteins (HCP) and/or viruses, while preserving the therapeutic protein within the product stream.

Purification can also involve one or more chromatography techniques (e.g., affinity, ion exchange, hydrophobic interaction), lectin-based purification, boronate-based purification, and/or filtration techniques (e.g., ultrafiltration) that are used as a capture step in separating the product from smaller impurities and/or as a concentration step in reducing the overall volume.

Optionally, polishing steps can also be performed in order to, for example, remove viruses, aggregated protein, and any other impurities before storing the therapeutic protein. The polishing steps can include, for example, virus filtration, hydrophobic interaction chromatography, and/or filtration steps (e.g., ultrafiltration/diafiltration and/or sterile filtration).

Accordingly, in some embodiments, the methods and systems provided herein involve purifying the therapeutic protein.

5.6. Methods and Systems for Determining Glycosylation and/or Glycation.

Figure 6:
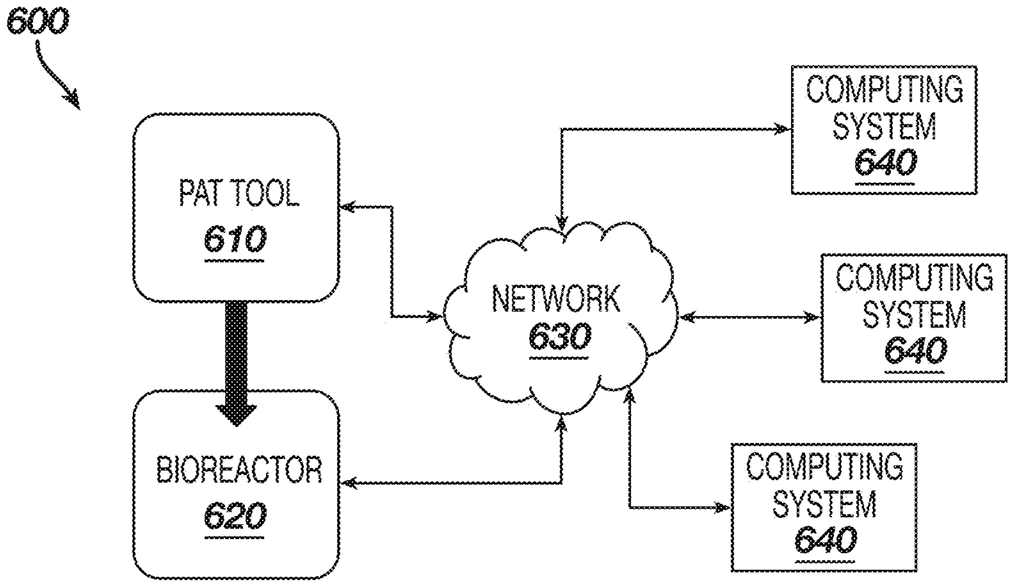
FIG. 6 illustrates an exemplary system for process flow diagram 600 illustrating an exemplary system used to provide the real time monitoring of glycation and/or glycosylation profiles of therapeutic proteins in manufacturing scale bioreactors.

With reference to diagram 600 of FIG. 6, the current subject matter can utilize a process analytical technology (PAT) tool 610 that can have a probe 612 that is either internal or extends into a bioreactor 620 to monitor or otherwise characterize aspects of reactions occurring within the bioreactor 620. The PAT tool 610 comprises one or more data processors and memory into which instructions can be loaded and executed by the data processors. The PAT tool 610 can take various forms and, in some cases, utilizes or otherwise comprises Raman spectroscopy to characterize aspects of the reactions occurring within the bioreactor 620. In some cases, the PAT tool 610 communicates over a network 630 with one or more computing systems 640 (e.g., servers, personal computers, tablets, IoT devices, mobile phones, dedicated control units, etc.) which can execute various algorithms as described below. The computing systems 640 can also act to change one or more operating parameters associated with the bioreactor 620. In some cases, the bioreactor 620 can also have network connectivity such that it can communicate with one or more remote computing systems 640 which, in turn, can cause one or more operating parameters of the bioreactor 620 to change.

The PAT tool 610 as noted above can be used to control and monitor production processes (such as in the bioreactor 620) in-line or at-line in real time. The PAT tool 610 can utilize spectroscopic techniques such as, for example, near-infrared spectroscopy, fluorescence spectroscopy and Raman spectroscopy. Raman spectroscopy presents itself as a technology particularly suited for use in bioreactor production processes as it provides clear, sharp spectra without suffering from some of the disadvantages of other technologies such as water interference in near-infrared spectroscopy and other interferences which might make the spectra less sharp and the like. The PAT tool 610 can include a laser to implement Raman spectroscopy which is a vibrational spectroscopic technique to provide a chemical fingerprint of a substance. The PAT tool 610 in the current context is technically advantageous in that it can provide non-destructive real time measurement of a number of biotherapeutic process variables including metabolites, growth profiles, product levels, product quality attributes, nutrient feeds, culture pH, and the like.

The computing systems 640 can combine Raman spectroscopic analysis from the PAT tool 610 with chemometric modelling to provide for the real time monitoring of these variables. The spectral peaks obtained by Raman spectroscopy are associated with one or more process variables of interest (which can be pre-defined and/or measured by offline analysis) using chemometric modelling software. Various signal processing techniques can be applied to identify and quantity the spectral peaks generated by the PAT tool 610. One type of signal processing technique is a Partial Least Squares (PLS) regression model which can be employed to model Raman data given the linear nature of the Raman signal vs. analyte concentration. In some embodiments, a linear PLS model can be employed. In certain embodiments, a nonlinear PLS model can be employed.

The PAT tool 610 can be used to measure or otherwise characterize aspects relating to large therapeutic proteins, such as mAb proteins, in the bioreactor 620. In particular, in some variations, the PAT tool 610 can be used to provide the real time monitoring of glycation and/or glycosylation profiles of therapeutic proteins in manufacturing scale bioreactors. Manufacturing scale presents many technical difficulties as opposed to smaller scale, laboratory bioreactors in that complex environmental conditions need to be addressed. The current subject matter addresses these technical difficulties as well as the intricate nature of glycoprotein formation by way of the utilized PAT tool 610 and, in some cases, the use of Raman-based PLS models.

Aspects of the PAT tool 610, the bioreactor 620, and/or the computing systems 640 herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and, may be implemented in a high-level procedural and/or object-oriented programming language, and/or in assembly/machine language. As used herein, the term "machine-readable medium" refers to any computer program product, apparatus and/or device (e.g., magnetic discs, optical disks, solid state drive, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The computing systems 640 can include a back-end component (e.g., as a data server), a middleware component (e.g., an application server), or a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet. The computing system 640 may include clients and servers.

A client and server are generally remote from each other and typically interact through a communication network. The relationship of client and server arises by virtue of computer programs running on the respective computers and having a client-server relationship to each other.

Figure 7:
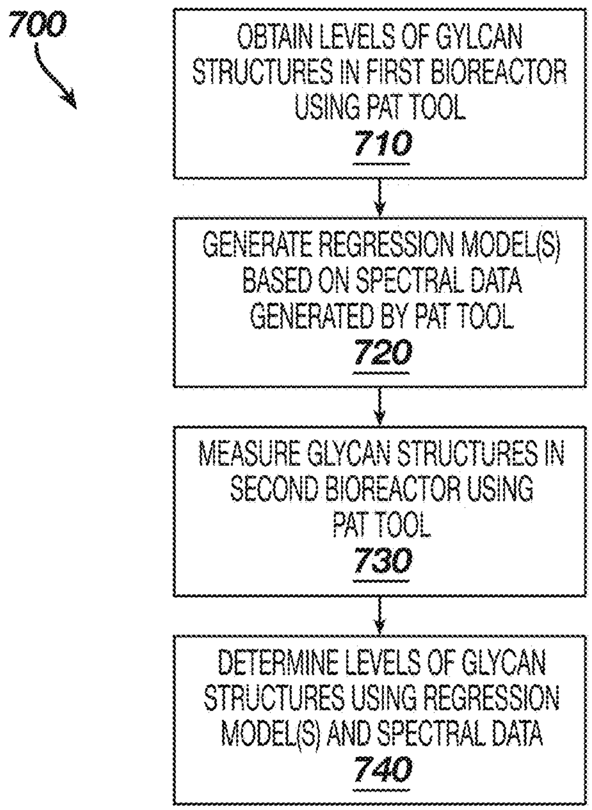
FIG. 7 illustrates a process flow diagram 700 depicting the determination of a glycan structure on a glycosylated molecule.

FIG. 7 is a process flow diagram 700 illustrating the determination of a glycan structure on a glycosylated molecule in which, at 710, levels are obtaining for one or more glycan structures on the glycosylated molecule, for each of a plurality of runs, using a process analytical technology (PAT) tool which obtains or otherwise generates spectral data. The levels are obtained based on processes occurring within one or more bioreactors having a volume equal to or below a first threshold. Thereafter, at 720, one or more regression models are generated based on the obtained spectral data that correlate levels of the one or more glycan structures on the glycosylated molecule with the obtained spectral data. Later, at 730, the one or more glycan structures on the glycosylated molecule are measured using the PAT tool within one or more second bioreactors having a volume equal to or above a second threshold to result in measured spectral data. At least one computing device then determines, at 740, levels of the one or more glycan structures on the glycosylated molecule within one or more bioreactors using the generated one or more regression models and based on the measured spectral data.

The one or more regression models can be refined based on the combination of the obtained spectral data and the measured spectral data.

One or more operating parameters of the one or more second bioreactors can be maintained and/or selectively modified (i.e., changed) based on the determined levels to produce a desired glycosylated molecule. The one or more operating parameters comprise a pH level, a nutrient level, a culture media concentration, a frequency interval for culture media addition, or a combination thereof. The nutrient level is selected from the group consisting of: a concentration of glucose, a concentration of lactate, a concentration of glutamine, and a concentration of ammonium ions. The concentration of glucose in the bioreactor can be automatically modified based on the measured spectral data.

In some variations, the glycosylated molecule can be purified.

The glycan structure can take various forms including G0F-GlcNac, G0, G0F, G1F, and G2F, or a combination thereof.

In some variations, the measurements can be conducted using two or more bioreactors having different volumes.

The first threshold can be of different volumes including about 25 liters or less.

The second threshold can correspond to different volumes including about 1,000 liters or more including 2,000 liters, 10,000 to about 25,000 liters, and to about 15,000 liters.

The second threshold can be at least 5× greater than the first threshold, and in some cases at least 10× greater than the first threshold, and in some cases, at least 100× greater than the first threshold, and in other cases at least 500× greater than the first threshold.

The PAT tool can utilize spectroscopic techniques including Raman spectroscopy.

The one or more regression models can include or otherwise use a partial least squares (PLS) model.

The glycosylated molecule can include a monoclonal antibody (mAb). Alternatively, the glycosylated molecule comprises a non-mAb.

The determination can be performed on-site and/or off-site. Further, the measuring and/or the determining can be performed in-line, at-line, on-line, off-line, or a combination thereof.

Figure 8:
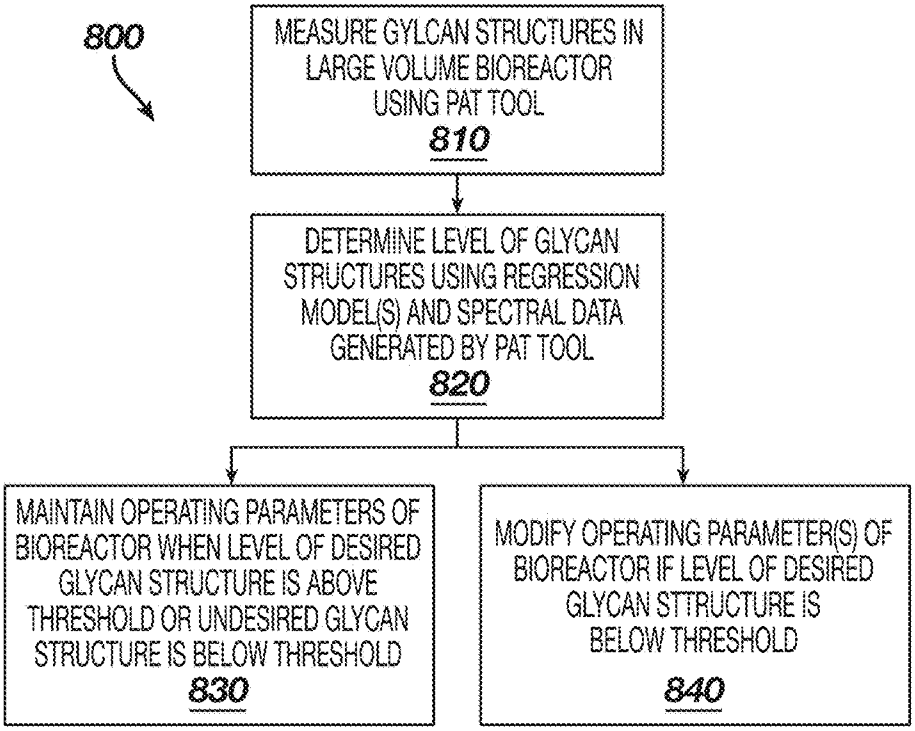
FIG. 8 illustrates a process flow diagram 800 depicting the production of a glycosylated molecule having a desired glycan structure.

FIG. 8 is a process flow diagram 800 illustrating the production of a glycosylated molecule having a desired glycan structure. One or more glycan structures are measured, at 810, using a process analytical technology (PAT) tool to result in spectral data. Such measuring is within a bioreactor having a volume of equal to or above 1,000 liters. Subsequently, at 820, a level of the one or more glycan structures within the bioreactor is determined by at least one computing device using one or more regression models and based on the measured spectral data. The one or more regression models are generated using trial runs from at least one bioreactor having a volume less than or equal to 50 liters and at least one bioreactor having a volume equal to or above 1,000 liters. One or more operating parameters of the bioreactor are maintained, at 830, when the level of a desired glycan structure is above a pre-defined threshold, or the level of an undesired glycan structure is below a pre-defined threshold. Further, at 840, one or more operating parameters of the bioreactor are modified when the level of a desired glycan structures is below a pre-defined threshold, or the level of an undesired glycan structure is above a pre-defined threshold.

Figure 9:
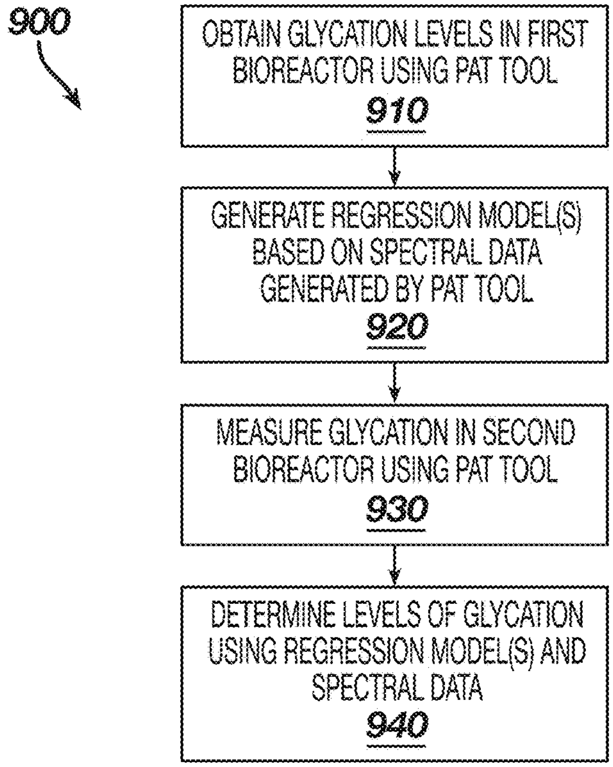
FIG. 9 illustrates a process flow diagram 900 depicting the determination of glycation on a molecule.

FIG. 9 is a process flow diagram 900 for determining glycation on a molecule. Glycation levels on the molecule are obtained, at 910, for each of a plurality of runs using a process analytical technology (PAT) tool. The obtaining can be within one or more bioreactors having a volume equal to or below a first threshold. The PAT tool can obtain or otherwise generate spectral data. One or more regression models are generated, at 920, based on the obtained spectral data that correlate glycation levels on the molecule with the obtained spectral data. Glycation on the molecule can then be measured, at 930, using the PAT tool. The measuring can be within one or more second bioreactors having a volume equal to or above a second threshold to result in measured spectral data. Later, at 940, glycation levels on the molecule within one or more bioreactors are determined by at least one computing device using the generated one or more regression models and based on the measured spectral data.

The one or more regression models can be refined based on the combination of the obtained spectral data and the measured spectral data.

One or more operating parameters of the one or more second bioreactors can be maintained and/or selectively modified (i.e., changed) based on the determined levels to produce a glycation level on the molecule. The one or more operating parameters comprise a pH level, a nutrient level, a culture media concentration, a frequency interval for culture media addition, or a combination thereof. The nutrient level is selected from the group consisting of: a concentration of glucose, a concentration of lactate, a concentration of glutamine, and a concentration of ammonium ions. The concentration of glucose in the bioreactor can be automatically modified based on the measured spectral data.

In some variations, the measurements can be conducted using two or more bioreactors having different volumes.

The first threshold can be of different volumes including about 25 liters or less.

The second threshold can correspond to different volumes including about 1,000 liters or more including 2,000 liters, 10,000 to about 25,000 liters, and to about 15,000 liters.

The second threshold can be at least 5× greater than the first threshold, and in some cases at least 10× greater than the first threshold, and in some cases, at least 100× greater than the first threshold, and in other cases at least 500× greater than the first threshold.

The PAT tool can utilize spectroscopic techniques including Raman spectroscopy.

The one or more regression models can include or otherwise use a partial least squares (PLS) model.

The molecule can include or be a mAb. Alternatively, the molecule includes or is a non-mAb.

The determination can be performed on-site and/or off-site. Further, the measuring and/or the determining can be performed in-line, at-line, on-line, off-line, or a combination thereof.

Figure 10:
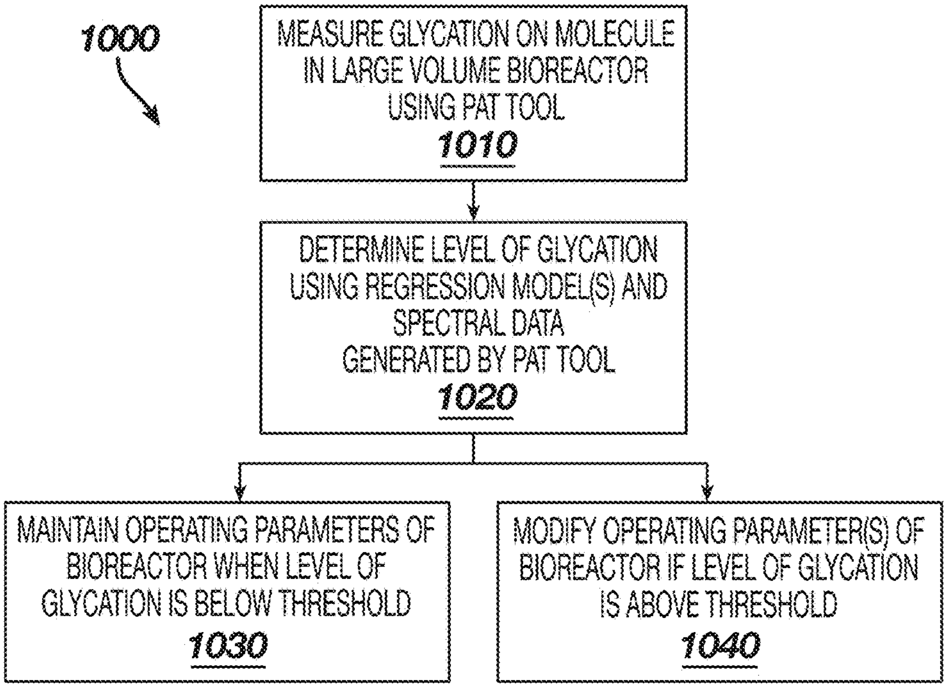
FIG. 10 illustrates a process flow diagram 1000 depicting production of a molecule with a desired level of glycation.
Figure 11A:
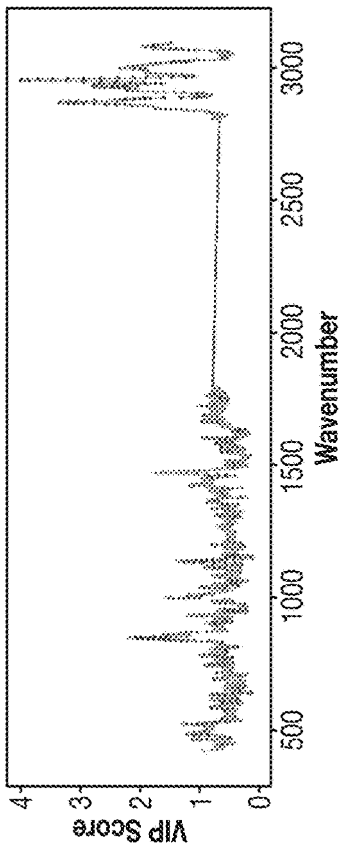
FIG. 11A-FIG. 11F illustrate an overlay of trends for variable importance of projections (VIP) scores of PLS models for (FIG. 11A) monoglycation/non-glycation, (FIG. 11B) G0F-GlcNac, (FIG. 11C) G0, (FIG. 11D) G0F, (FIG. 11E) G1F, and (FIG. 11F) G2F (in flow 1 and flow 3.
Figure 11B:
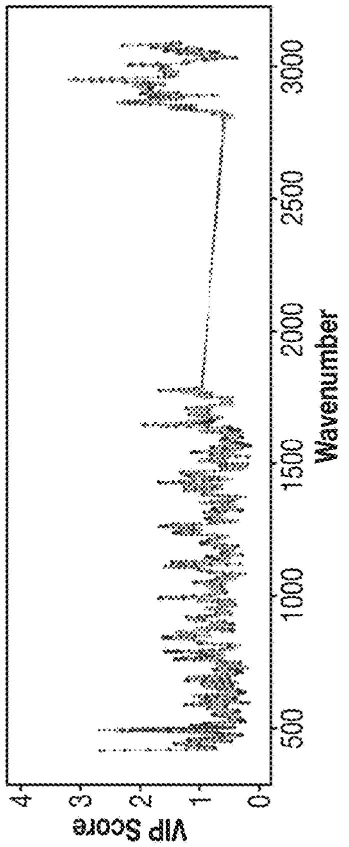
Figure 11C:
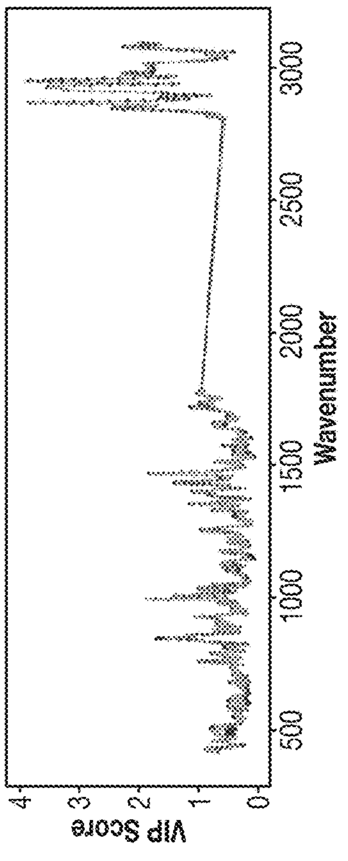
Figure 11D:
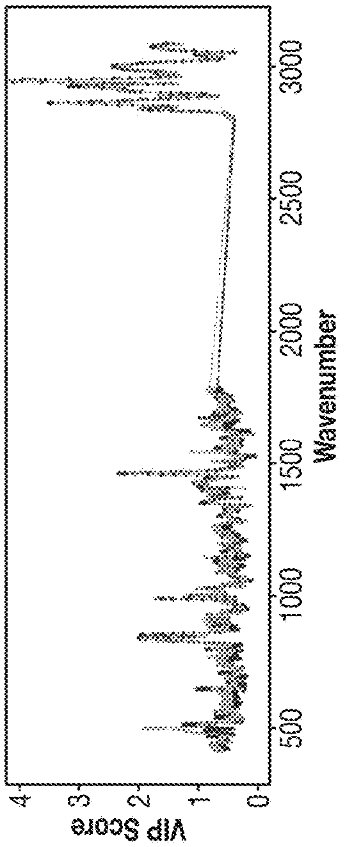
Figure 11E:
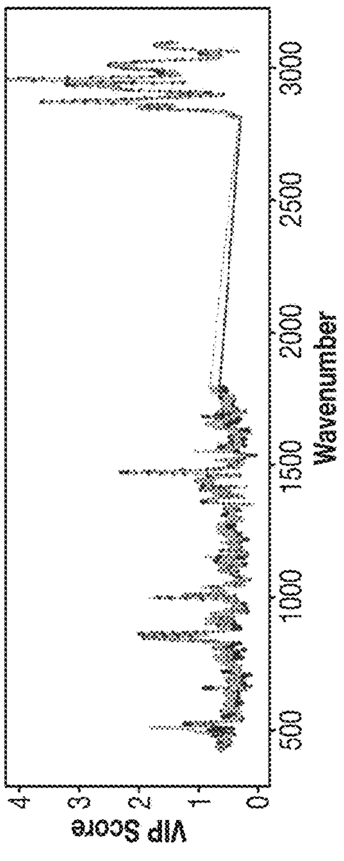
Figure 11F:
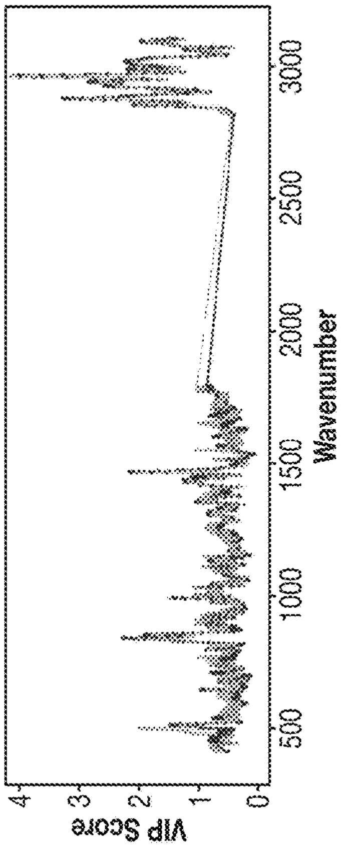

FIG. 10 is a process flow diagram 1000 illustrating production of a molecule with a desired level of glycation. Glycation on the molecule is measured, at 1010, using a process analytical technology (PAT) tool to result in spectral data. The measuring can be within a bioreactor having a volume of equal to or above 1,000 liters. Later, at 1020, levels of glycation on the molecule within the bioreactor are determining, by at least one computing device using one or more regression models and based on the measured spectral data. The one or more regression models can be generated using trial runs from at least one bioreactor having a volume less than or equal to 50 liters and at least one bioreactor having a volume equal to or above 1,000 liters. One or more operating parameters of the bioreactor are maintained, at 1030, when the level of glycation on the molecule is below a pre-defined threshold. In addition, at 1040, on or more operating parameters of the bioreactor are selectively modified when the level of glycation on the molecule is above a pre-defined threshold.

6. EMBODIMENTS

A1. A method for determining a glycan structure on a glycosylated molecule, the method comprising:

- obtaining, for each of a plurality of runs, levels for one or more glycan structures on the glycosylated molecule using a process analytical technology (PAT) tool, wherein the obtaining is within one or more first bioreactors having a first volume equal to or below a first threshold, the PAT tool obtaining spectral data;
- generating one or more regression models based on the obtained spectral data that correlate levels of the one or more glycan structures on the glycosylated molecule with the obtained spectral data;
- measuring the one or more glycan structures on the glycosylated molecule using the PAT tool, wherein the measuring is within one or more second bioreactors having a second volume equal to or above a second threshold to result in measured spectral data; and
- determining, by at least one computing device using the generated one or more regression models and based on the measured spectral data, levels of the one or more glycan structures on the glycosylated molecule within one or more second bioreactors.

A2. The method of embodiment A1, further comprising refining the one or more regression models based on the combination of the obtained spectral data and the measured spectral data.

A3. The method of embodiment A1 or embodiment A2, further comprising maintaining one or more operating parameters of the one or more second bioreactors based on the determined levels to produce a desired glycosylated molecule.

A4. The method of embodiment A1 or embodiment A2, further comprising selectively modifying one or more operating parameters of the one or more second bioreactors based on the determined levels to produce a desired glycosylated molecule.

A5. The method of embodiment A4, wherein the one or more operating parameters comprise a pH level, a nutrient level, a culture media concentration, a frequency interval for culture media addition, or a combination thereof.

A6. The method of embodiment A5, wherein the nutrient level is selected from the group consisting of: a concentration of glucose, a concentration of lactate, a concentration of glutamine, and a concentration of ammonium ions.

A7. The method of embodiment A6, wherein the concentration of glucose is automatically modified based on the measured spectral data.

A8. The method of any one of embodiments A1 to A7, further comprising purifying the glycosylated molecule.

A9. The method of any one of embodiments A1 to A8, wherein the glycan structure is selected from the group consisting of: G0F-GlcNac, G0, G0F, G1F, and G2F, or a combination thereof.

A10. The method of any one of embodiments A1 to A9, wherein the obtaining is within two or more bioreactors having different volumes.

A11. The method of any one of embodiments A1 to A10, wherein the first threshold is about 250 liters or less.

A12. The method of any one of embodiments A1 to A10, wherein the first threshold is about 100 liters or less.

A13. The method of any one of embodiments A1 to A10, wherein the first threshold is about 50 liters or less.

A14. The method of any one of embodiments A1 to A10, wherein the first threshold is about 25 liters or less.

A15. The method of any one of embodiments A1 to A10, wherein the first threshold is about 10 liters or less.

A16. The method of any one of embodiments A1 to A10, wherein the first threshold is about 5 liters or less.

A17. The method of any one of embodiments A1 to A10, wherein the first threshold is about 2 liters or less.

A18. The method of any one of embodiments A1 to A10, wherein the first threshold is about 1 liter or less.

A19. The method of any one of embodiments A1 to A18, wherein the second threshold is about 1,000 liters or more.

A20. The method of any one of embodiments A1 to A18, wherein the second threshold is about 2,000 liters or more.

A21. The method of any one of embodiments A1 to A18, wherein the second threshold is about 5,000 liters or more.

A22. The method of any one of embodiments A1 to A18, wherein the second threshold is about 10,000 to about 25,000 liters.

A23. The method of any one of embodiments A1 to A18, wherein the second threshold is about 15,000 liters.

A24. The method of any one of embodiments A1 to A18, wherein the second threshold is at least 5× greater than the first threshold.

A25. The method of any one of embodiments A1 to A18, wherein the second threshold is at least 10× greater than the first threshold.

A26. The method of any one of embodiments A1 to A18, wherein the second threshold is at least 100× greater than the first threshold.

A27. The method of any one of embodiments A1 to A18, wherein the second threshold is at least 500× greater than the first threshold.

A28. The method of any one of embodiments A1 to A27, wherein the first volume is about 0.5 to about 250 liters.

A29. The method of any one of embodiments A1 to A27, wherein the first volume is about 1 to about 50 liters.

A30. The method of any one of embodiments A1 to A27, wherein the first volume is about 1 to about 25 liters.

A31. The method of any one of embodiments A1 to A27, wherein the first volume is about 1 to about 10 liters.

A32. The method of any one of embodiments A1 to A27, wherein the first volume is about 1 to about 5 liters.

A33. The method of any one of embodiments A1 to A32, wherein the second volume is about 1,000 to about 25,000 liters.

A34. The method of any one of embodiments A1 to A32, wherein the second volume is about 2,000 to about 25,000 liters.

A35. The method of any one of embodiments A1 to A32, wherein the second volume is about 5,000 to about 25,000 liters.

A36. The method of any one of embodiments A1 to A32, wherein the second volume is about 10,000 to about 25,000 liters.

A37. The method of any one of embodiments A1 to A32, wherein the second volume is about 15,000 to about 25,000 liters.

A38. The method of any one of embodiments A1 to A37, wherein the PAT tool utilizes or otherwise comprises Raman spectroscopy.

A39. The method of any one of embodiments A1 to A38, wherein the one or more regression models comprise a partial least squares (PLS) model.

A40. The method of any one of embodiments A1 to A39, wherein the glycosylated molecule comprises a monoclonal antibody (mAb).

A41. The method of any one of embodiments A1 to A40, wherein the glycosylated molecule comprises a non-mAb.

A42. The method of any one of embodiments A1 to A41, wherein the determining step is performed on-site.

A43. The method of any one of embodiments A1 to A41, wherein the determining step is performed off-site.

A44. The method of any one of embodiments A1 to A43, wherein the determining step is performed in-line, at-line, on-line, off-line, or a combination thereof.

A45. The method of any one of embodiments A1 to A44, wherein the determining step is performed on-line.

A46. The method of any one of embodiments A1 to A44, wherein the determining step is performed at-line.

A47. The method of any one of embodiments A1 to A44, wherein the determining step is performed off-line.

A48. The method of any one of embodiments A1 to A44, wherein the determining step is performed in-line.

A49. The method of any of the preceding embodiments, wherein the obtaining comprises: receiving data characterizing the spectral data from the PAT tool.

A50. The method of any of the preceding embodiments, wherein the generating is executed by one or more computing devices.

B1. A method of producing a glycosylated molecule having a desired glycan structure, the method comprising:

measuring one or more glycan structures using a process analytical technology (PAT) tool to result in spectral data, wherein the measuring is within a bioreactor having a volume of equal to or above 1,000 liters;

determining, by at least one computing device using one or more regression models and based on the measured spectral data, a level of the one or more glycan structures within the bioreactor, wherein the one or more regression models are generated using trial runs from at least one bioreactor having a volume less than or equal to 50 liters and at least one bioreactor having a volume equal to or above 1,000 liters; and maintaining one or more operating parameters of the bioreactor when:

the level of a desired glycan structure is above a pre-defined threshold, or the level of an undesired glycan structure is below a pre-defined threshold; and selectively modifying one or more operating parameters of the bioreactor when:

the level of a desired glycan structures is below a pre-defined threshold, or the level of an undesired glycan structure is above a pre-defined threshold.

B2. The method of embodiment B1, wherein measuring is performed in-line, at-line, on-line, off-line, or a combination thereof.

B3. The method of embodiment B1 or embodiment B2, wherein measuring is performed in-line.

B4. The method of embodiment B1 or embodiment B2, wherein measuring is performed at-line.

B5. The method of embodiment B1 or embodiment B2, wherein measuring is performed off-line.

B6. The method of embodiment B1 or embodiment B2, wherein measuring is performed on-line.

B7. The method of any one of embodiments B1 to B6, wherein measuring occurs more than once daily.

B8. The method of any one of embodiments B1 to B6, wherein measuring occurs about every 5 to 60 minutes.

B9. The method of any one of embodiments B1 to B6, wherein measuring occurs about every 10 to 30 minutes.

B10. The method of any one of embodiments B1 to B6, wherein measuring occurs about every 10 to 20 minutes.

B11. The method of any one of embodiments B1 to B6, wherein measuring occurs about every 12.5 minutes.

B12. The method of any one of embodiments B1 to B11, wherein the bioreactor volume is about 2,000 liters or more.

B13. The method of any one of embodiments B1 to B11, wherein the bioreactor volume is about 5,000 liters or more.

B14. The method of any one of embodiments B1 to B11, wherein the bioreactor volume is about 10,000 liters or more.

B15. The method of any one of embodiments B1 to B11, wherein the bioreactor volume is about 15,000 liters or more B16. The method of any one of embodiments B1 to B11, wherein the bioreactor volume is about 10,000 liters to about 25,000 liters.

B17. The method of any one of embodiments B1 to B11, wherein the bioreactor volume is about 15,000 liters.

B18. The method of any one of embodiments B1 to B17, wherein the determining step is performed on-site.

B19. The method of any one of embodiments B1 to B17, wherein the determining step is performed off-site.

B20. The method of any one of embodiments B1 to B19, wherein the desired glycan structure is selected from the group consisting of: G0F-GlcNac, G0, G0F, G1F, and G2F, or a combination thereof.

B21. The method of any one of embodiments B1 to B20, wherein bioreactor is a batch reactor, a fed-batch reactor, a perfusion reactor, or a combination thereof.

B22. The method of any one of embodiments B1 to B21, wherein the one or more operating parameters comprise a pH level, a nutrient level, a culture media concentration, a frequency interval for culture media addition, or a combination thereof.

B23. The method of embodiment B22, wherein the nutrient level is selected from the group consisting of: a concentration of glucose, a concentration of lactate, a concentration of glutamine, and a concentration of ammonium ions.

B24. The method of embodiment B23, wherein the concentration of glucose is automatically modified based on the measured spectral data.

B25. The method of any one of embodiments B1 to B24, wherein the PAT tool utilizes or otherwise comprises Raman spectroscopy.

B26. The method of any one of embodiments B1 to B25, wherein the one or more regression models comprise a partial least squares (PLS) model.

C1. A system for producing one or more glycosylated molecules comprising,

- means for culturing a glycosylated molecule-producing cell line;
- means for measuring a level of one or more glycan structures, wherein the means generates spectral data;
- means for generating one or more regression models based on the spectral data; and
- means for measuring a level of one or more glycan structures in a glycosylated molecule-producing cell line.

C2. The system of embodiment C1, wherein the glycosylated molecule-producing cell line is a mammalian cell line.

C3. The system of embodiment C2, wherein the mammalian cell line is a non-human cell line.

C4. The system of any one of embodiments C1 to C3, wherein the culturing comprises batch, fed-batch, perfusion, of a combination thereof.

C5. The system of any one of embodiments C1 to C4, wherein culturing comprises a volume of about 2,000 liters or more.

C6. The system of any one of embodiments C1 to C4, wherein culturing comprises a volume of about 5,000 liters or more.

C7. The system of any one of embodiments C1 to C4, wherein culturing comprises a volume of about 10,000 liters or more.

C8. The system of any one of embodiments C1 to C4, wherein culturing comprises a volume of about 15,000 liters or more.

C9. The system of any one of embodiments C1 to C4, wherein culturing comprises a volume of about 10,000 liters to about 25,000 liters.

C10. The system of any one of embodiments C1 to C4, wherein culturing comprises a volume of about 15,000 liters.

C11. The system of any one of embodiments C1 to C4, wherein measuring is performed in-line, at-line, on-line, off-line, or a combination thereof.

C12. The system of any one of embodiments C1 to C11, wherein measuring is performed in-line.

C13. The system of any one of embodiments C1 to C11, wherein measuring is performed on-line.

C14. The system of any one of embodiments C1 to C11, wherein measuring is performed at-line.

C15. The system of any one of embodiments C1 to C11, wherein measuring is performed off-line.

C16. The system of any one of embodiments C1 to C15, wherein measuring occurs more than once daily.

C17. The system of any one of embodiments C1 to C15, wherein measuring occurs about every 5 to 60 minutes.

C18. The system of any one of embodiments C1 to C15, wherein measuring occurs about every 10 to 30 minutes.

C19. The system of any one of embodiments C1 to C15, wherein measuring occurs about every 10 to 20 minutes.

C20. The system of any one of embodiments C1 to C15, wherein measuring occurs about every 12.5 minutes.

C21. The system of any one of embodiments C1 to C20, wherein the one or more glycan structures are selected from the group consisting of: G0F-GlcNac, G0, G0F, G1F, and G2F, or a combination thereof.

C22. The system of any one of embodiments C1 to C21, further comprising a means for selectively modifying one or more operating parameters to enhance production of a desired one or more glycan structures.

C23. The system of embodiment C22, wherein the one or more operating parameters comprise a pH level, a nutrient level, a culture media concentration, a frequency interval for culture media addition, or a combination thereof.

C24. The system of embodiment C23, wherein the nutrient level is selected from the group consisting of: a concentration of glucose, a concentration of lactate, a concentration of glutamine, and a concentration of ammonium ions.

C25. The system of embodiment C24, wherein the concentration of glucose is automatically modified based on the spectral data.

C26. The system of any one of embodiments C1 to C25, wherein the one or more glycosylated molecules comprise a monoclonal antibody (mAb).

C27. The system of any one of embodiments C1 to C25, wherein the one or more glycosylated molecules comprise a non-mAb.

C28. The system of any one of embodiments C1 to C27, the spectral data comprises Raman spectra.

C29. The system of any one of embodiments C1 to C28, wherein the one or more regression models comprise a partial least squares (PLS) model.

C30. The system of any one of embodiments C1 to C29, further comprising a means for isolating the one or more glycosylated molecules.

D1. A system for producing one or more glycosylated molecules:

- a bioreactor comprising a glycosylated molecule-producing cell line;
- a process analytical technology (PAT) tool that measures one or more glycan structures and generates spectral data; and
- a processor that correlates levels of one or more glycan structures with the spectral data using one or more regression models.

D2. The system of embodiment D1, wherein the bioreactor is about 2,000 liters or more.

D3. The system of embodiment D1, wherein the bioreactor is about 5,000 liters or more.

D4. The system of embodiment D1, wherein the bioreactor is about 10,000 liters or more.

D5. The system of embodiment D1, wherein the bioreactor is about 15,000 liters or more.

D6. The system of embodiment D1, wherein the bioreactor is about 10,000 liters to about 25,000 liters.

D7. The system of embodiment D1, wherein the bioreactor is about 15,000 liters.

D8. The system of any one of embodiments D1 to D7, wherein the glycan structure is selected from the group consisting of: G0F-GlcNac, G0, G0F, G1F, and G2F, or a combination thereof.

D9. The system of any one of embodiments D1 to D8, wherein the glycosylated molecule-producing cell line is a mammalian cell line.

D10. The system of embodiment D9, wherein the mammalian cell line is a non-human cell line.

D11. The system of any one of embodiments D1 to D10, wherein the PAT tool utilizes or otherwise comprises Raman spectroscopy.

D12. The system of any one of embodiments D1 to D11, wherein the one or more regression models comprise a partial least squares (PLS) model.

7. EXAMPLES

The following examples of the application are to further illustrate the nature of the application. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Example 1: Experimental Design for Real Time Monitoring of Glycation and Glycosylation The purpose of this study was to develop PLS models of Raman spectra for real time monitoring of glycation and glycosylation (both CQAs), in a representative CHO cell culture at manufacturing scale.

Model development from reduced scale data was initially assessed. Developing model robustness was then considered by supplementing the reduced scale data with manufacturing scale data. Product quality was considered throughout the manufacturing process of the biotherapeutic mAb product, by using Raman Spectroscopy to achieve this by monitoring CQAs in real time throughout the upstream production process.

Eighteen batches of a mAb-producing CHO cell line were used in the experimental design. The stirred bioreactor scales were single use bag (SUB) 2000 L (Thermo Fisher Scientific, Waltham, MA), glass 5 L (Applikon Inc., Schiedam, Netherlands) and glass 1 L (Eppendorf, Hamburg, Germany) and the fed-batch process lasted for 16-18 days. In total, nine 1 L batches, seven 5 L and two 2000 L batches were included. Each 2000 L batch was inoculated on Day 0 using a commercial seed train, ten reduced scale bioreactors were inoculated using Day 1 cell culture from a 2000 L batch and six reduced scale bioreactors were inoculated on Day 0 using a laboratory seed train. Basal media and daily feed media were used for each batch executed, and process controls for all were implemented.

Two feeding strategies were employed during execution of the bioreactor runs, each consisted of two complex feeds, starting on Day 3 to each bioreactor. Twelve batches (2×2000 L, 7×5 L, 3×1 L) were fed both complex feeds daily based upon a defined percentage of the vessel volume. The other 6 batches (6×1 L) were fed the first complex feed based upon a defined percentage of the vessel and the second complex feed was delivered multiple times in a day to maintain a predefined target level of glucose in the bioreactor as part of a feed strategy study. All bioreactors were inoculated within the same seeding density limits.

Each batch had identical control targets for dissolved oxygen (DO), pH, and temperature. DO was controlled to 40% by aeration and sparged oxygen. A pH target of 6.95 was maintained using addition(s) of carbon dioxide and 2.0 M sodium carbonate. Temperature was controlled to the set point of 36.5° C. (35.5° C.-37.5° C.) throughout the cell culture. The scale-dependent process parameter agitation was transferred across scales using power per volume-calculated values. Offline samples were collected daily from each bioreactor and measured for a panel of metabolites including glucose, Lactate, titer, viable cell density and % viability using the Vi-CELL MetaFLEX (Beckman Coulter, Brea, CA), Vi-CELL XR Cell Viability Analyzer (Beckman Coulter) and Cedex Bio (Roche Holding AG, Switzerland) offline analysers. Each daily culture sample was retained and frozen at −70° C. for further testing once each batch had been completed.

Glycation and Glycosylation Analysis

Glycation and glycosylation of the mAbs were characterized offline by LC/MS analysis. Briefly, protein samples for glycation analysis were first pretreated with EndoS enzyme to remove N-linked carbohydrates in order to eliminate glycoform based sample heterogeneity. The protein samples were then separated by High Performance Liquid Chromatography (HPLC) and analyzed by online electrospray ionization quadrupole time-of-flight mass spectrometry. Mass/charge data collected across the chromatographic peak was then summed and deconvoluted using Empower software (Waters Corp, Milford, MA). Detected glycation Isoforms were assigned based on deconvoluted mass spectra analysis and their relative abundance were calculated using peak intensities of centered deconvoluted mass spectra. Protein samples for glycosylation were first pretreated with 1M Dithiothreitol to separate individual mAb heavy and light chains. The protein samples were then analyzed as before by LC/MS and the glycosylation isoforms assigned and quantified as described previously.

Raman Spectral Acquisition During Bioreactor Batches

Raman spectra were gathered using two instruments for all batches with each using a multichannel Raman RXN2 system (Kaiser Optical Systems Inc., Ann Arbor, MI), which contained a 785-nm laser source and a charge-coupled device (CCD) at −40° C. The detector was connected to an MR probe, which consisted of a fiber optic excitation cable and a fiber optic collection cable (Kaiser Optical Systems Inc.). Data was collected by the MR probe attached to a bIO-Optic-220 stainless steel probe (Kaiser Optical Systems Inc.) inserted in the sterile bioreactor. The iCRaman software 4.1. (Mettler Toledo Autochem, Columbia, MD) was used to control the Raman RXN2 for spectral acquisition for all reduced scale batches (1 L, 5 L). The Raman Runtime HMI (Kaiser Optical Systems Inc.) was used for spectral acquisition in all 2000 L batches. Collection for all Raman spectral data used the system settings of 10-s exposures for 75 scans, which resulted in a spectrum for a probe after 15 min including an overhead time of 2.5 min. Raman spectral acquisition spanned from wavenumbers 100-3,425 cm-1. Reduced-scale vessels were protected from light interference by aluminum foil. (due to the single-use bioreactor set up in the manufacturing suite this was not required as it was enclosed in stainless steel). Intensity calibration of the instrument was performed with the Hololab Calibration Accessory (HCA) (Kaiser Optical Systems Inc.) prior to each use of the system and internal calibrations were set to occur every 24 hr throughout the bioreactor process.

Example 2: Development of Raman Spectroscopy Based PLS Models for Glycation and Glycosylation at Reduced Scale (Flow 1)

This example demonstrates that Raman spectroscopy based PLS models can be developed for glycation and glycosylation profiles of an exemplary therapeutic protein producing cell line during production in a bioreactor.

In this example, both Raman and offline data from the cell culture process at reduced scale (1 L and 5 L) was used to develop a panel of 7 chemometric PLS models for the glycation and glycosylation profiles of the mAb. Two models were considered for glycation (mono-glycated, non-glycated), and 5 models were considered for the glycosylation profile (G0F-GlcNac, G0, G0F, G1F, G2F). Chemometric modelling was performed with Simca 15.1 (Umetrics Inc., San Jose, CA).

Offline measurements for glycation and glycosylation were aligned with Raman spectra based on the time at which they were taken, beginning at Day05 in each batch. The decision to build models from this time point was based on empirical knowledge of the process and its production of mAb product at detectable levels by HPLC. All data prior to Day 05, Raman spectra and offline measurements, were excluded from model building and testing.

Each model consisted of a calibration sample set (CSS) of 15 batches (9×1 L and 6×5 L), for model development, and a calibration test sample set (CTSS) of 1 batch (5 L), used as a blind data set for testing with the PLS model generated for each CQA. This batch was chosen as the CTSS randomly from the available 5 L batch data. The X variables for each model in this flow were Raman spectra (centered) and the Y variables were Offline values for; % Mono-glycated, Non-glycated, G0F-GlcNac, G0, G0F, G1F and G2F (univariately scaled). Wavenumber selection of the Raman spectra for all models was 415-1800 cm-1 and 2800-3100 cm-1. The spectral filters applied to all PLS models were Savitsky-Golay first derivative quadratic (31 cm-1 point) and standard normal variate (SNV; data not shown).

Each PLS model was built and assessed for error by using a method of leave-batch-out cross validation (leave each batch out once in model development). The model error was averaged based upon prediction of the model against the omitted batch to identify the root mean square of cross-validation (RMSEcv). The RMSEcv indicates the predictive power of the model based on the data used to build the model. A lower average error (RMSEcv) indicated an improved model. This enabled better informed decision-making on which component number was to be used for the models generated for testing against the blind data set. Testing the models' predictive capability vs the CTSS, using the predict function in Simca 15.1, identified the root mean square error of prediction (RMSEP), which indicates the predictive power of the model vs an unseen dataset. The Regression (R2) value, coefficient of variation was recorded for each PLS model. This R2 value is used to determine the amount of variation of the Y variable which the model predictors (X variables) can explain. The closer an R2 value is to 1, the greater a model explained the Y variable. Model performance was assessed based on each models' respective RMSEcv, RMSEP and R2 values. The variable importance of projections (VIPs) of each model was also considered, this is a parameter which summarizes the importance of the X-variables in a model in predicting the Y-variable. X-Variables with a value greater than 1, are considered most relevant for explaining the Y-variable.

Flow 1 evaluated the use of reduced scale data only as a calibration data set for PLS model building. Each of the 7 models developed, 2 for glycation (Mono-glycated, Non-glycated) and 5 glycosylation profiles (G0F-GlcNac, G0, G0F, GIF, G2F) were tested by predicting against a blind data set of reduced scale batch data. Each model in flow 1 consisted of 15 batches of reduced scale process data in the CSS with one full batch (5 L) being used for testing as a blind CTSS.

Leave batch out cross validation was used to determine the optimum component number for each model. This was decided as the lowest number of components with the lowest matching RMSEcv value. Each model was assessed individually for optimum component number. Average R2 results from cross validation show a strong degree of variability in each model, explained by an R2 value of >0.8 reported for each of the models considered (Table 1). The acceptance criteria for each model's accuracy were determined based on the range of the measurements observed in the model CSS. Accuracy acceptance criteria was set as 10% of the range of the values used in the calibration data set as per chemometric model development 5 standards at JSI. This was determined to be an adequate acceptance criterion based on potential sources of error for each model including the acceptable error of the method employed in offline analysis. The error in each model was assessed by comparing the root mean square errors (RMSEcv, RMSEP) against the acceptance criteria calculated (Table 1). The RMSEcv informs the optimum component number. This value also indicates the ability of the model to predict the variable of interest based on the calibration dataset. The component numbers chosen for each model gave an RMSEcv which fell within the acceptance criteria for prediction error and as such were deemed appropriate for model development.

TABLE I

Flow 1: Model development statistics for Raman PLS models for glycation and glycosylation

| Cross-validation data set | | | | |
|---|---|---|---|---|
| CQA (%) | Component Number | $R^2$ | RMSECV | Acceptable RMSECV |
| Monoglycated | 6 | 0.8036 | 0.5169 | ≤0.554 |
| Non-Glycated | 6 | 0.8036 | 0.5169 | ≤0.554 |
| G0F-GlcNac | 6 | 0.9019 | 0.0312 | ≤0.0322 |
| G0 | 5 | 0.9348 | 0.1315 | ≤0.1453 |
| G0F | 6 | 0.9546 | 2.1576 | ≤2.6964 |
| G1F | 6 | 0.9570 | 2.0707 | ≤2.4149 |
| G2F | 5 | 0.9138 | 0.2670 | ≤0.3349 |
| **Blind Prediction data set (5 L)** | | | | |
| CQA (%) | Component Number | $R^2$ | RMSEP | Acceptable RMSEP |
| Monoglycated | 6 | 0.7131 | 0.5409 | ≤0.554 |
| Non-Glycated | 6 | 0.7131 | 0.5409 | ≤0.554 |
| G0F-GlcNac | 6 | 0.6945 | 0.0303 | ≤0.0322 |
| G0 | 5 | 0.8777 | 0.1611 | ≤0.1453 |
| G0F | 6 | 0.902 | 1.8996 | ≤2.6964 |
| G1F | 6 | 0.9163 | 1.756 | ≤2.4149 |
| G2F | 5 | 0.9115 | 0.2273 | ≤0.3349 |

Complimentary results were observed when each model's prediction accuracy was tested with the blind data set (5 L batch) (Table 1). The $R^2$ was >0.85 for Mono-glycated, Non-glycated, G0F, G1F, G2F, G0 and <0.7 G0F-GlcNac. All $R^2$ values showed a decrease when tested against the blind data set, however, the RMSEP values for all models, except for G0, mono-glycation and non-glycation, showed a lower error in prediction than the values observed for the RMSEcv. An $R^2$ of >0.9 does not necessarily indicate a better model and reinforces the need to consider multiple factors including RMSEcv and RMSEP in conjunction with $R^2$ values during model assessment.

While testing against the blind data set at reduced scale showed a decrease in $R^2$ and slight increase in model error observed for the G0, mono-glycation and non-glycation models, it should be noted that these models still falls within the acceptance criteria and so can be deemed suitable for use in predicting glycosylation at reduced scale. The trends observed for the prediction testing (FIG. 3A-FIG. 3G) confirm the suitability of the models for use, the Mono-glycated and Non-glycated trends follow the offline data trends tightly and are complementary to one another for the process duration as would be expected. G0F-GlcNac, G0, G0F, G1F and G2F follow the offline trends similarly and whilst slight deviations were observed in each, all were within acceptable error criteria.

Raman spectral regions identified in each model to have a VIP score >1 indicated an acceptable degree of model specificity (FIG. 11A-FIG. 11F). Glycation models (mono-glycated, non-glycated) indicated a Raman spectral region association similar to that identified for glucose PLS models previously, while some degree of secondary correlation is likely due to the structure of glycated proteins, unwanted correlations with glucose for these models was avoided by ensuring data used in the model CSS was acquired at intervals both pre and post glucose feeding. Different glucose feeding strategies were also employed when executing bioreactor batches for data collection in order to break unwanted glucose correlations. The glycosylation profile models (G0F-GlcNac, G0, G0F, G1F, and G2F) showed VIP scores >1 in regions which have previously been associated with glycan components, for example, mannose, fucose, n-acetylglucosamine. This suggests the model identifying peaks in the Raman spectra associated with each of the glycans.

An initial assessment of the inner relation plot of each model indicated a satisfactory level of linearity to progress with model assessment, however it is possible for future work, given secondary correlations with product titer, a nonlinear-PLS method could potentially improve model accuracy. Model performance in each case is acceptable and a close agreement with daily offline samples with an expected profile supports model development decisions made in this flow.

The ability to monitor CQAs such as glycation and glycosylation in real time during a bioreactor process aligns with the key goals of QbD, with the assessment of quality being built into the process (PDA, 2012). Using in process CQA monitoring, a cause and effect relationship can be established between the critical process parameters (CPPs) and product quality. Establishing this approach early in product development when process characterization has not yet been fully completed can reduce the time needed for development and scale up (Kozlwoski, 2006) as well as reducing manufacturing inefficiencies which allow for tighter control of product quality and an improvement in yield (Yu et al., 2014).

The results presented here support the decisions made in model development and show that Raman spectroscopy based PLS models are capable of predicting both the glycation profiles and glycosylation, with specific focus on glycan profiles, of CHO mAb producing bioreactor processes.

Example 3: Prediction of Glycation and Glycosylation at Manufacturing Scale Using Models Developed with Reduced Scale Data (Flow 2)

In this example, each of the models developed using the CSS described above in Example 2 were investigated for their capability to accurately predict at manufacturing scale. No adjustments or additional data were used to develop the models in this example.

Each model (Mono-glycated, Non-glycated, G0F-GlcNac, G0, G0F, G1F and G2F) was tested and evaluated by using the predict function in Simca 15.1 against a new CTSS comprised of data from a single manufacturing scale batch (2000 L Batch A) for this cell culture process. This batch was chosen as the CTSS randomly from the available 2000 L batch data. The CTSS was then used to investigate the ability of Raman models developed using only reduced scale data (1 L, 5 L) to predict CQAs at a manufacturing scale. A leave batch out cross validation was not repeated as there were no changes made to the models, and as such no change to RMSEcv was observed. Each of the 7 model's RMSEP and R2 values were compared to the outputs of models generated in Example 2 to determine whether reduced scale data alone is sufficient for PLS model development.

In flow 2, model robustness was tested against manufacturing scale data (2000 L). Each model from flow 1 described above in Example II was tested by predicting against a new blind CTSS comprised of process data from a 2000 L batch. The model statistics for RMSEcv were as observed in Flow 1 as no additional data was added or removed from the models. Average $R^2$ values of >0.80 were observed when predicted against the 2000 L blind dataset in the case of all models (Table 2) indicating good variability within each model.

TABLE 2

Flow 2: Model development statistics for Raman PLS models for glycation and glycosylation.

| Cross-validation data set | | | | |
|---|---|---|---|---|
| CQA (%) | Component Number | $R^2$ | RMSECV | Acceptable RMSECV |
| Monoglycated | 6 | 0.8036 | 0.5169 | ≤0.554 |
| Non-Glycated | 6 | 0.8036 | 0.5169 | ≤0.554 |
| G0F-GlcNac | 6 | 0.9019 | 0.0312 | ≤0.0322 |
| G0 | 5 | 0.9348 | 0.1315 | ≤0.1453 |
| G0F | 6 | 0.9546 | 2.1576 | ≤2.6964 |
| G1F | 6 | 0.9570 | 2.0707 | ≤2.4149 |
| G2F | 5 | 0.9138 | 0.2670 | ≤0.3349 |

| Blind Prediction data set | | | | |
|---|---|---|---|---|
| CQA (%) | Component Number | $R^2$ | RMSEP | Acceptable RMSEP |
| Monoglycated | 6 | 0.8699 | 0.3553 | ≤0.554 |
| Non-Glycated | 6 | 0.8699 | 0.3553 | ≤0.554 |
| G0F-GlcNac | 6 | 0.8544 | 0.0272 | ≤0.0322 |
| G0 | 5 | 0.8334 | 0.0997 | ≤0.1453 |
| G0F | 6 | 0.9317 | 2.6670 | ≤2.6964 |
| G1F | 6 | 0.9447 | 2.3687 | ≤2.4149 |
| G2F | 5 | 0.8916 | 0.4074 | ≤0.3349 |

The glycation models both performed well, with an RMSEP of 0.3553% observed in the case of each model (Mono-glycated and Non-glycated). Surprisingly, the RMSEP values observed here were lower than were observed in flow 1 (described in Example 2). This would indicate that reduced scale data alone may be sufficient to develop a model for monitoring glycation profiles of therapeutic protein (e.g., mAb) processes. The interactions that lead to protein glycation are dependent on the levels of reducing sugars, temperature and time in the bioreactor (Quan et al., 2008). While the specific glycation site occupancy can be difficult to control (Wei et al., 2017), the overall level of glycation can be maintained at certain levels during production scale up. As such, the process variables which typically contribute to glycation are maintained at a comparable level across all bioreactor scales. For this reason, using reduced scale data may be sufficient in developing robust glycation models.

Statistics relating to the glycosylation models show a more varied response when tested against the manufacturing scale data. The RMSEP value for the G2F model was observed to be 0.4074% which was outside of the acceptance criteria and accordingly the model was deemed unsuitable for use in monitoring at manufacturing scale. Interestingly, the $R^2$ value for this model was >0.85, further reinforcing the importance of consulting multiple statistics when evaluating PLS models.

Figures 4A, 4B, 4C, 4D, 4E, 4F, 4G:
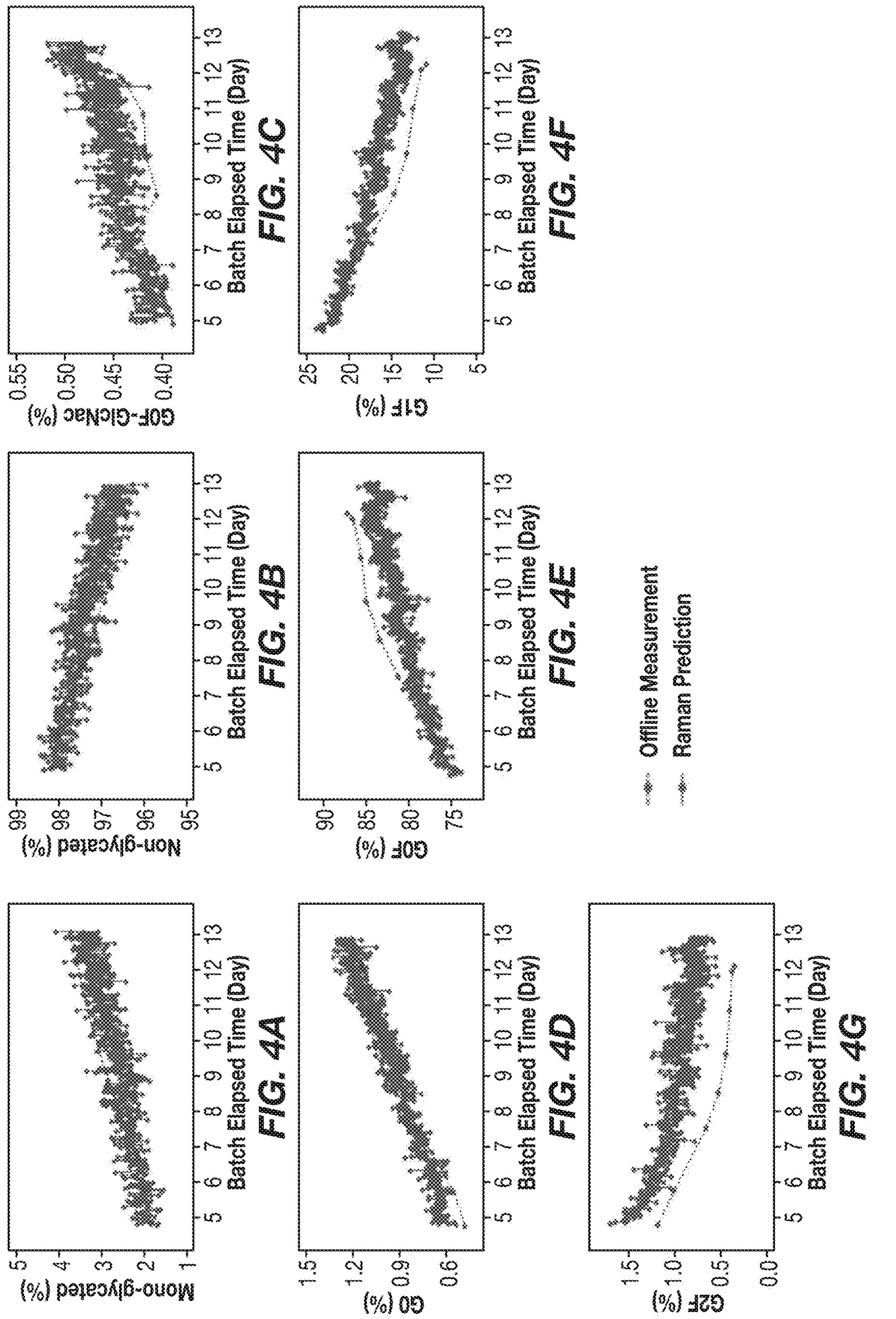
FIG. 4A-FIG. 4G illustrate Raman PLS model predictions (fluctuating blue line) vs. offline measurements (steady red line) for mono-glycation (FIG. 4A), non-glycation (FIG. 4B), G0F-GlcNac (FIG. 4C), G0 (FIG. 4D), G0F (FIG. 4E), G1F (FIG. 4F), and G2F (FIG. 4G) in manufacturing scale (2,000 L) batch (CTSS) without adding or removing additional data from the models.

The trends showing the Raman model predictions vs the offline values for the 2000 L batch as it progressed (FIG. 4A-FIG. 4G) confirm the model statistics, with the G2F deviating from the offline measurement trends for the entirety of the batch (FIG. 4G). The G0F-GlcNac, G0, G0F, G1F models met the acceptance criteria and visually appear to follow the trends of the offline measurements. G0 and G0F-GlcNac performed best with a comparable or lower RMSEP value vs that obtained in flow 1. G0F and G1F showed a noticeable increase in RMSEP value and it was observed from the trends (FIG. 4E and FIG. 4F, respectively) that the predictive capability of these models begins to decline past day 07 in the process. Existing knowledge indicates that the process moves from the exponential growth phase to the stationary phase at day 07/08. As CHO cell cultures progress and move into the stationary phase of growth they reach peak antibody production. Cell size and metabolic rates change with the cells increasing in product output by as much as twice the rate in the exponential growth phase (Templeten et al., 2013; Xiao et al., 2017).

The models presented in flow 2 would indicate that the process changes occurring at this time point have a different effect on the glycosylation profiles at reduced scale vs manufacturing scale. Even after introducing variability into the models using spectra at multiple scales (1 L and 5 L), different Raman probes/optics, different glucose feed strategies (6×1 L) and glucose spikes (1×5 L), it was found that the predictive capability of the models based on reduced scale data only was not robust at a manufacturing scale.

Taking the models as a combined profile, glycosylation models built using reduced scale data perform worse when predicting against manufacturing data with an increase in prediction error observed in G0, G1F and G2F. G2F, in particular, had a significant increase (79%) in prediction error putting it outside the acceptable limits for prediction error (RMSEP). While reduced scale bioreactor processes are designed to be representative of the manufacturing process, it is apparent here that the glycosylation kinetics at manufacturing scale differ to a degree whereby reduced scale data is not alone adequate for robust PLS model development.

Example 4: Inclusion of Manufacturing Scale Data into Raman Spectroscopy Based PLS Models for Predicting Glycation and Glycosylation at Manufacturing Scale (Flow 3)

This example describes the use of an updated CSS which is comprised of the CSS data from the small scale experiments described above in Example 2, and supplemented with data from a single manufacturing scale (2000 L Batch B) batch to build each PLS model. Calibration dataset for models developed in flow 1 (described above in Example 2) were supplemented with a single batch of manufacturing scale data (2000 L) and prediction testing was carried out as per flow 2 (described above in Example 3), using the same 2000 L blind CTSS.

The CSS of 16 batches (9×1 L, 6×5 L and 1×2000 L) was then used to develop 7 updated models as per Example 2. Once completed, each of the 7 models was then assessed by leave batch out cross validation in order to derive an updated RMSEcv and component number for each model. Testing the models' predictive capability vs the new CTSS, using the predict function in Simca 15.1, identified the root mean square error of prediction (RMSEP) and the R2 value for the updated models. As in previous flows, the RMSEcv, RMSEP, R2, and VIP values output from each model were assessed to identify the models' ability to predict at manufacturing scale. They were also used to compare predictive capability against the models developed and used in flow 1 and flow 2 to determine the necessity of including manufacturing scale data in the CSS of Raman PLS models for glycation and glycosylation.

The models here (Flow 3) sought to investigate the impact of scale data on the predictive power and robustness of the models constructed in flow 1 (described above in Example 2). The models from flow 1 were supplemented with process data from a 2000 L scale batch run. The addition of this 2000 L batch data meant that 16 batches were used to develop each model. Cross validation was again used here to determine the optimum component number for model development and prediction testing. An average R e value of >0.8 was observed at cross validation for all models with each model also having an RMSEcv within the acceptable criteria (Table 3).

TABLE 3

Flow 3: Model development statistics for Raman PLS models for glycation and glycosylation Cross-validation data set

| CQA (%) | Component Number | $R^2$ | RMSECV | Acceptable RMSECV |
|---|---|---|---|---|
| Monoglycated | 6 | 0.8029 | 0.5132 | ≤0.554 |
| Non-Glycated | 6 | 0.8029 | 0.5132 | ≤0.554 |
| G0F-GlcNac | 6 | 0.9007 | 0.0311 | ≤0.0322 |
| G0 | 5 | 0.9312 | 0.1313 | ≤0.1453 |
| G0F | 6 | 0.9517 | 2.1541 | ≤2.6964 |
| G1F | 6 | 0.9535 | 2.0647 | ≤2.4149 |
| G2F | 5 | 0.9316 | 0.2669 | ≤0.3349 |

Blind Prediction data set (2000L)

| CQA (%) | Component Number | $R^2$ | RMSEP | Acceptable RMSEP |
|---|---|---|---|---|
| Monoglycated | 6 | 0.8992 | 0.3279 | ≤0.554 |
| Non-Glycated | 6 | 0.8992 | 0.3279 | ≤0.554 |
| G0F-GlcNac | 6 | 0.8171 | 0.0224 | ≤0.0322 |
| G0 | 5 | 0.8424 | 0.0977 | ≤0.1453 |
| G0F | 6 | 0.9302 | 1.50925 | ≤2.6964 |
| G1F | 6 | 0.9438 | 1.43486 | ≤2.4149 |
| G2F | 5 | 0.9147 | 0.0919 | ≤0.3349 |

For this flow, the prediction testing was completed using the manufacturing scale blind test data set from flow 2. An average $R^2$ of >0.80 was observed for each model. Notably, all models showed a decrease in the RMSEP value indicating a reduced error in prediction across all models. Also the RMSEcv of each model was observed to be similar or slightly reduced for each model which would signal that the addition of manufacturing scale data to these models did not impact the models ability to predict at small scale. The G2F model was greatly improved when the CSS was supplemented with manufacturing scale data, as evidenced by a reduction in RMSEP from 0.4074% to 0.0919% (a relative improvement in prediction error of 77.5%). Moreover, the trends seen in FIG. 5A-FIG. 5G illustrate that the deviations observed in flow 2 (see FIG. 4A-FIG. 4G) have been accounted for and the models were able to accurately predict throughout the entire manufacturing scale process.

The regions of each model with VIP score >1 were compared to the models created in flow 1, each model designated similar or the same regions as significant contributors to the model, in some cases the score for the regions identified changed as a result of the manufacturing scale data addition, which further supported the decisions made during model development (FIG. 11A-FIG. 11F). It should be noted that during this work models for both mono-glycation and non-glycation were developed, each model shared the same results across all three flows. As a result a single model could be created, and the complimentary result inferred. For the purpose of this work, both models were created in an effort to support the decisions made in model development and show that acceptable values were obtained in each case when testing against an unknown dataset.

Taken together, the results presented here highlight the importance of model robustness and the considerations which must be taken into account when designing model calibration data sets. Moreover, the inclusion of manufacturing scale data, while in this study only representative of 4.4% of the total data observations available for use in the CSS, results in a significant improvement in the model's predictive power and helps ensure robust model development.

Example 5: Assessment of the Impact of Raman Based Glucose Feedback Control on Cell Bioreactor Process Development The aim of this study was to investigate the impact that a continuous Raman based feedback control strategy, using a GMP ready PAT management tool, has on cell bioreactor processes (e.g., a CHO cell bioreactor process). As exemplary models, two CHO cell bioreactor processes were chosen based on their respective development stage and the development strategy. The impact of the Raman based feedback control strategy on each CHO cell bioreactor process was considered in terms of cellular growth, metabolism and productivity, as well as a number of key process parameters and quality attributes when compared to bolus fed bioreactor processes. The results demonstrate that Raman spectroscopy is an effective PAT tool in process development and optimization.

Example 5.1: Materials and Methods

Bioreactor Operation. Two mAb-producing CHO cell lines (Cell Line 1, Cell Line 2) were used in the experimental design. Three bioreactor batches of Cell Line 1 (Batch A, Batch B, Batch C) and three bioreactor batches of Cell Line 2 (Batch D, Batch E, Batch F), were executed in light shielded 1 L bioreactors (Eppendorf, Hamburg, Germany) with the process for each cell line lasting 14-15 days. Each batch was inoculated on Day 0, within the same seeding density limits, from a seed train that was propagated using media and targets. Basal media and feed media were used for each batch and process controls. Cell Line 1 was used as a standard cell line for normal yield. Cell Line 2 was used as a high output cell line that has higher growth rate and resource demand.

Two feeding strategies were employed during each of the bioreactor runs. The feeding strategy for Cell Line 1 consisted of a complex feed and glucose feed. Batch A was bolus fed both complex and glucose feeds once per day, starting on Day 3, based upon a defined percentage of the vessel volume. Batch B and Batch C were fed the complex feed once per day, starting on Day 3, based upon a defined percentage of the vessel and the glucose feed was automated and delivered as required, based on the Raman glucose value, to maintain a predefined target level of 1 g/l glucose in the bioreactor, which was determined a posteriori. The feeding strategy for Cell Line 2 consisted of two complex feeds and a glucose feed. Batch D was bolus fed both complex feeds and glucose feed once per day, starting on Day 3. The complex feeds were delivered using a defined percentage of the vessel volume and the glucose feed was based on achieving a defined glucose target concentration for that day. Batch E and Batch F were fed both complex feeds once per day, starting on Day 3, as a defined percentage of the vessel and the glucose feed was automated and delivered as required, based on the Raman glucose value, to maintain a predefined target level of 2 g/l glucose in the bioreactor, which was also determined a posteriori. Each batch had identical control targets for dissolved oxygen (DO), pH, and temperature. DO was controlled to 40% by aeration and sparged oxygen. A pH target of 6.95 was maintained using addition(s) of carbon dioxide and 2.0 M sodium carbonate. Temperature was controlled to the set point of 36.5° C. (35.5° C.-37.5° C.) throughout the cell culture.

Evaluation of Bioreactor Performance: Offline Sample Analysis and Online Parameter Trending. Offline samples were collected daily from each bioreactor and measured for glucose, lactate, titer, viable cell density and % viability using the Vi-CELL MetaFLEX (Beckman Coulter, Brea, CA), Vi-CELL XR Cell Viability Analyzer (Beckman Coulter) and Cedex Bio (Roche Holding AG, Switzerland) offline analyzers. Each daily culture sample was retained and frozen at −70° C. for further testing once each batch had been completed.

Glycation was considered when evaluating the impact of glucose feedback control. Offline samples from day 4-day 14/15 for each of the six bioreactor batches were thawed for product quality analysis of the mAbs produced throughout the batch. Glycation of the mAbs was characterized offline by LC/MS analysis. Briefly, all samples were initially purified using protein A purification. Protein samples for glycation analysis were then pretreated with EndoS enzyme to remove N-linked carbohydrates in order to eliminate glycoform based sample heterogeneity. The protein samples were then separated by Ultra-High Performance Liquid Chromatography (HPLC) using Waters Acquity UPLC system (Waters Corp, Milford, MA) on a reverse phase column using a gradient of acetonitrile with trifluoroacetic acid and analyzed with a Xevo G2-XS Mass Spectrometer (Waters Corp, Milford, MA) by online electrospray ionization quadrupole time-of-flight mass spectrometry. Mass/charge data collected across the chromatographic peak was then summed and deconvoluted using Masslynx (Agilent Technologies, Santa Clara, CA) or UNIFI software (Waters Corp, Milford, MA). Detected glycation isoforms were assigned based on deconvoluted mass spectra analysis and their relative abundances were calculated using peak intensities of centered deconvoluted mass spectra.

Online trends for both pH and O2 delivery were trended and compared throughout batch execution for both cell lines, using Dasware control software (Hamburg, Germany), as key indicators of bioreactor environment and process conditions in the bioreactor. An evaluation of both online and offline data provided indication for any process differences observed when automated feedback control of glucose was used.

Raman Spectral Acquisition. Raman spectra were gathered for each batch using a multichannel Raman RXN2 system (Kaiser Optical Systems Inc., Ann Arbor, MI), which contained a 785-nm laser source and a charge-coupled device (CCD) at −40° C. The detector was connected to an MR probe, which consisted of a fiber optic excitation cable and a fiber optic collection cable (Kaiser Optical Systems Inc.). Data was collected by the MR probe attached to a bIO-Optic-220 stainless steel probe (Kaiser Optical Systems Inc.) inserted in the sterile bioreactor. The Raman Runtime HMI (Kaiser Optical Systems Inc.) was used for spectral acquisition in all batches. Collection of all Raman spectral data used the system settings of 10s exposures for 75 scans, which resulted in a spectrum for a probe after 15 min including an overhead time of 2.5 min. Raman spectral acquisition spanned from wavenumbers 100-3,425 cm-1. Reduced-scale vessels were protected from light interference by aluminum foil. Intensity calibration of the instrument was performed with the Hololab Calibration Accessory (Kaiser Optical Systems Inc.) prior to each use of the system and internal calibrations were set to occur every 24 hr throughout the bioreactor process.

Raman based PLS model development for Glucose. A cell line specific Raman based glucose PLS model was developed for Cell Line 1 and Cell Line 2 in this study to facilitate real time generation of glucose concentrations in the bioreactor and to facilitate the execution of real time feedback control for glucose. All chemometric modelling was performed with SIMCA 15.0 (Umetrics Inc., San Jose, CA). Offline measurements for glucose were aligned with Raman spectra based on the time at which they were taken. Each model consisted of a calibration sample set (CSS) of reduced scale and manufacturing scale data, where available. The Cell Line 1 model CSS consisted of 12 batches (6×5 L, 3×2000 L and 3×1 L), for model development, and a calibration test sample set (CTSS) of 1 batch (1 L), was used as a blind data set for testing with the PLS model. This batch was chosen as the CTSS randomly from the available batch data at 1 L scale. The Cell Line 2 model CSS consisted of 7 batches (3×5 L and 4×1 L), for model development, and a calibration test sample set (CTSS) of 1 batch (1 L), was used as a blind data set for testing with the PLS model. This batch was chosen as the CTSS randomly from the available batch data at 1 L scale. The CTSS was chosen as a 1 L batch as this was the scale at which both models would be deployed for real time feedback control. All model development data was collected from lab scale studies and manufacturing scale batches executed previously. For each of the PLS models generated, robustness within the CSS was ensured by including both process and technology variability. A varied sampling strategy was employed in a number of batches included in the CSS in order to break any spurious correlations with batch progression.

The X variables for each model were Raman spectra (centered) and the Y variables were Offline values for glucose (univariately scaled). Wavenumber selection of the Raman spectra for each model was 415-1800 cm-1 and 2800-3100 cm-1. The spectral filters applied to each PLS model were Savitsky-Golay first derivative quadratic (15 cm-1 point) and standard normal variate (SNV; data not shown). Each PLS model was built and assessed for error by using a method of leave-batch-out cross validation (leave each batch out once in model development). The model error was averaged based upon prediction of the model against the omitted batch to identify the root mean square error of cross-validation (RMSEcv). The RMSEcv indicates the predictive power of the model based on the data used to build the model. A lower average error (RMSEcv) indicated an improved model. This enabled better informed decision—making on which component number was to be used for the models generated for testing against the blind data set. Each model was also assessed using the root mean square error of estimation (RMSEE), a model performance indicator which relates to the residuals of the data points in the CSS, i.e. the fit of the model. Testing the models' predictive capability vs the CTSS, using the predict function in Simca 15.1, identified the root mean square error of prediction (RMSEP), which indicates the predictive power of the model vs an unseen dataset. The Regression ($R^2$) value, coefficient of variation was recorded for each PLS model. This $R_2$ value is used to determine the amount of variation of the Y variable which the model predictors (X variables) can explain. The closer an R2 value is to 1, the greater a model explained the Y variable. Model performance was assessed based on each models' respective RMSEE, RMSEcv, RMSEP and R2 values.

Implementation of Raman based feedback control of Glucose. The automation of glucose feeding was facilitated by a PAT management tool, synTQ (Optimal Industrial Automation Limited, UK). Briefly, an orchestration (recipe) created within synTQ linked the Raman Instrument to the Glucose PLS model and the bioreactor system to execute feedback control. Initiation of the orchestration in synTQ signaled the Raman Instrument to begin acquiring spectral data via Open Platform Communication (OPC) connection. The spectral data generated was then sent to synTQ where it was subsequently fed into the Glucose PLS model which is contained in a SIMCA Q engine block of the orchestration. The spectral data is translated into a glucose reading for each point where spectral data is generated which was subsequently used to calculate the glucose feed to be delivered, within the orchestration. The resulting calculation of the glucose feed was then communicated from synTQ to the Dasware bioreactor control software (Eppendorf, Germany), to start and stop the glucose feed pumps on the bioreactor system after the feed had been delivered, via OPC connection. The glucose target concentration was maintained by initiating a glucose feed to the target concentration each time the Raman and glucose model data indicated that the glucose concentration in the bioreactor had dropped below the target value. This process was repeated, for each Raman spectra generated, for the duration of the batch.

Example 5.2: Results

Raman based PLS model development for Glucose. Prior to execution of glucose feedback control batches, Raman based PLS models were developed using Raman spectra and offline glucose data which had been collected from previously completed batches. A cell line specific glucose model was developed for Cell Line 1 and Cell Line 2. The Cell Line 1 model contained 170 data points in its CSS and the Cell Line 2 model contained 169 data points in its CSS. A leave batch out cross validation approach was used for determining the optimum component number for each model.

Figure 12A:
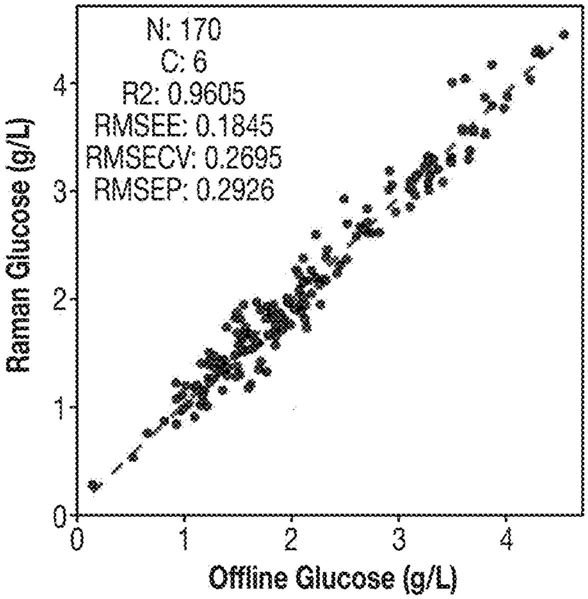
FIG. 12A-FIG. 12B illustrate plot of Raman glucose values vs offline glucose values for CSS of Glucose model for (FIG. 12A) Cell Line 1 and (FIG. 12B) Cell Line 2.
Figure 12B:
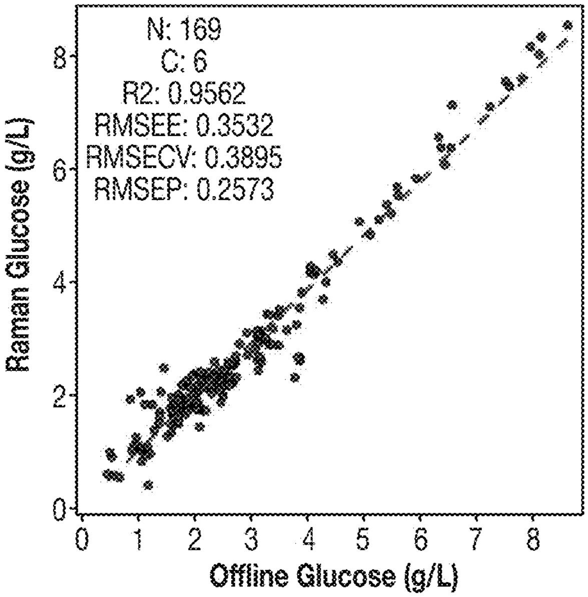

FIG. 12A and FIG. 12B summarize the finalized model for each cell line, the RMSEE for the Cell Line 1 glucose model was 0.1845 g/l and was 0.3532 g/l for the Cell Line 2 glucose model. The RMSEE values coupled with R2 values for both models >0.95 indicated that there was strong variability within each model and serves to support the decisions made in the data included in each model CSS. The acceptable accuracy criteria for prediction of each model was determined to be <0.5 g/l. This was determined in relation to the current glucose feed targets employed in each Cell Line bioreactor process.

For process control purposes, a glucose measurement outside of this range may have a negative influence on the process as it may result in over or underfeeding of the bioreactor. As such, the accuracy for each model was further verified in terms of the alignment of the RMSEcv and RMSEP of each glucose model to the acceptance criteria. Both the Cell Line 1 and Cell Line 2 models were determined to have an optimum component number of 6, with corresponding RMSEcv value of 0.2695 g/l and 0.3895 g/l, respectively. The component numbers chosen for each model gave an RMSEcv which fell within the acceptance criteria for prediction error indicating the ability of the model to predict the variable of interest based on the calibration dataset and as such were deemed appropriate for model development. Complimentary RMSEP values were observed when each of the models were tested against their respective CTS S. The Cell Line 1 glucose model had an RMSEP of 0.2926 g/l and the Cell Line 2 model had an RMSEP of 0.2573 g/l. Both of these values were well within the acceptance criteria established (≤0.5 g/l) for model development. Good agreement between the model statistics indicated that the design considerations made in development for both models was justified and ensured each model was robust and would accurately predict and control glucose levels in each cell line's bioreactor process.

The model CSS for Cell Line 1 and 2 differ in the availability of data at the time of model creation due to differences in the stage of process development of each cell line. A manufacturing scale batch was available for inclusion in the Cell Line 1 model whereas only lab scale data was available for the Cell Line 2 model. Despite this, both models were developed with an acceptable degree of accuracy for the purpose of this work. The Cell Line 1 model may be more easily scaled up in its current state, while the Cell Line 2 model may require additional data and model adjustment. The availability of additional data collected at the manufacturing scale can improve these models for in line deployment at scale.

Implementation of Raman based feedback control of glucose. For this study an automated feedback control strategy which maintained glucose to a predefined setpoint concentration was considered. Two cell lines were chosen to test this strategy and each strategy was executed in duplicate and compared to the currently employed strategy for each cell line, which was a once daily bolus feed in both cell lines. Each study was executed using a single Raman instrument and as such spectral acquisition was limited to once every ~45 mins. This was determined to be an acceptable interval for automated feedback control of glucose based on previous data generated for process setpoints and glucose consumption rates for each of the cell lines considered.

Figure 13A:
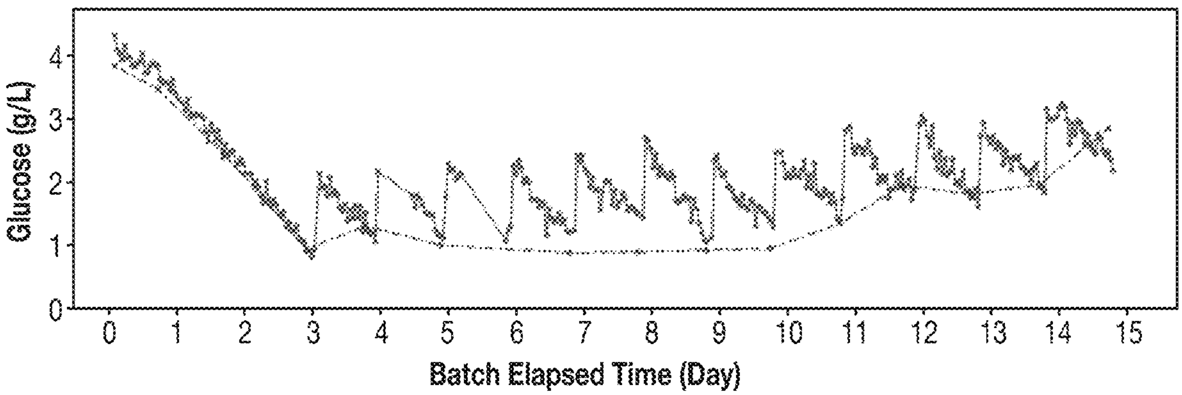
FIG. 13A-FIG. 13C illustrate Raman PLS model predictions (fluctuating blue line) vs. offline measurements (steady red line) for Cell Line 1, (FIG. 13A) Batch A: Bolus Fed, (FIG. 13B) Batch B: automated feedback control to 1 g/l, (FIG. 13C) Batch C: automated feedback control to 1 g/l.
Figure 13B:
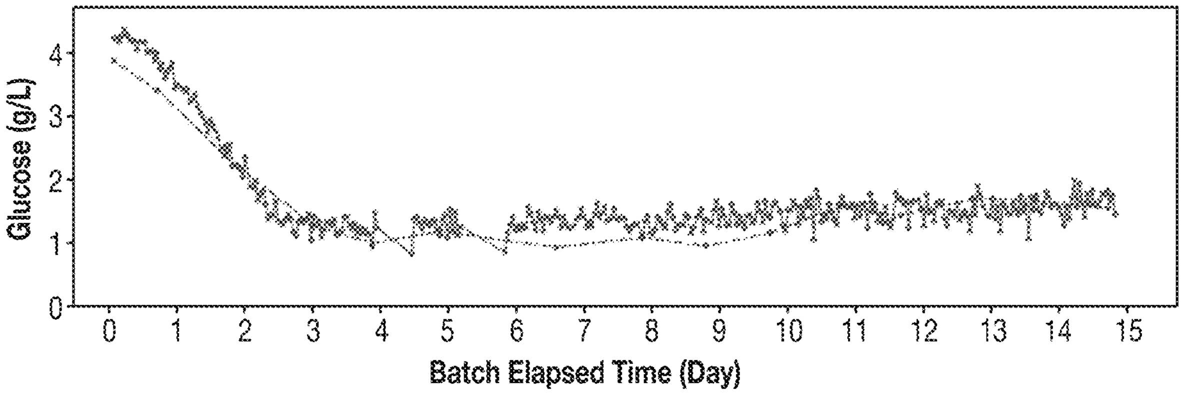
Figure 13C:
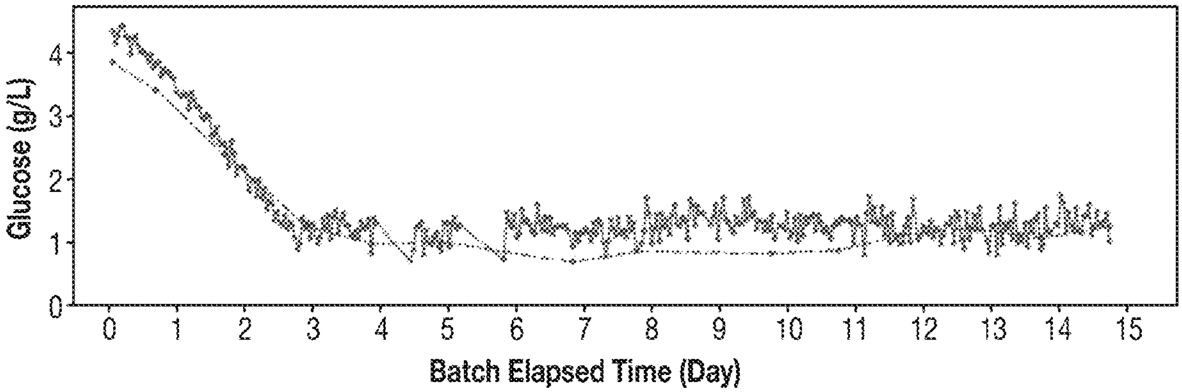

The glucose trends for the Cell Line 1 batches are outlined in FIG. 13A-FIG. 13C. FIG. 13A shows the Raman glucose trend for the bolus fed batch for Cell Line 1, Batch A. The Raman measurement of glucose throughout the batch performed well with an observed RMSEP of 0.2917 g/l. The Raman measurement provides a much greater insight into the glucose trends and consumption throughout this batch and was used to indicate whether manual delivery of glucose had sufficiently hit the target for each feed event. It was observed in Batch A that a bolus feed strategy for glucose results in a large daily spike of glucose when feeding occurs, beginning on Day 03, which would not be observed if using offline daily measurements only. This shows that there is additional process information available when using Raman as a PAT tool even in the case where it is not controlling feed delivery that would otherwise be unavailable to a process development team. The glucose concentration throughout Batch A fluctuates between 1-3 g/l.

In contrast, the automated feedback control batches for Cell Line 1, Batch B and Batch C, FIG. 13A and FIG. 13C show a much tighter feeding profile with the glucose concentration maintaining at 1 g/l throughout each batch. The initiation of feeding began on Day 03 in each automated feedback control batch that is comparable to the timing of the initial bolus feed for Batch A. No large spikes in concentration were observed and a consistent glucose concentration was maintained for 12 days. The RMSEP for Batch B and C were 0.2887 g/l and 0.2940 g/l respectively, a low RMSEP in each case here further serves to indicate that the glucose model for Cell Line 1 was strong and performed well. A low RMSEP in each case indicated that the model was able to provide an accurate indication of the glucose concentration for the process and informed feed delivery well, within the established acceptance criteria of +/−0.5 g/L.

Figure 14A:
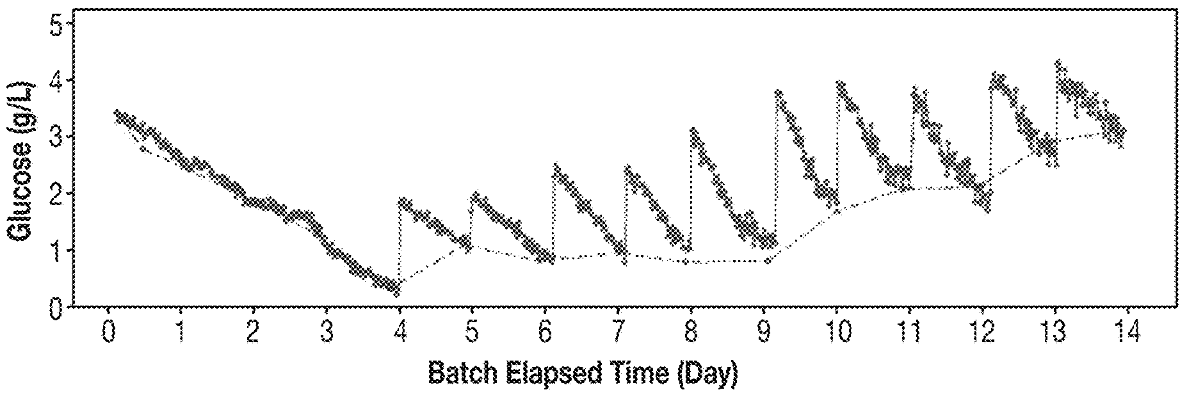
FIG. 14A-FIG. 14C illustrate Raman PLS model predictions (fluctuating blue line) vs. offline measurements (steady red line) for Cell Line 2, (FIG. 14A) Batch D: Bolus Fed, (FIG. 14B) Batch E: automated feedback control to 2 g/l, (FIG. 14C) Batch F: automated feedback control to 2 g/l.
Figure 14B:
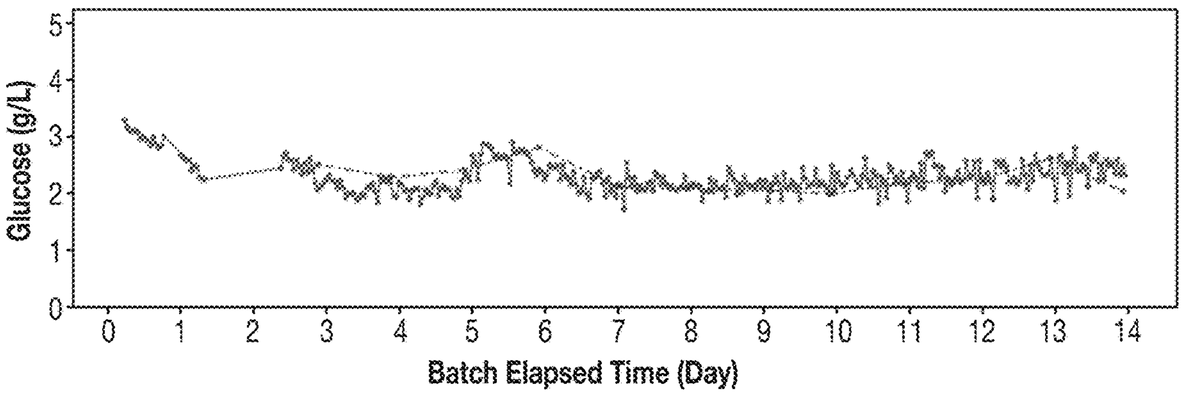
Figure 14C:
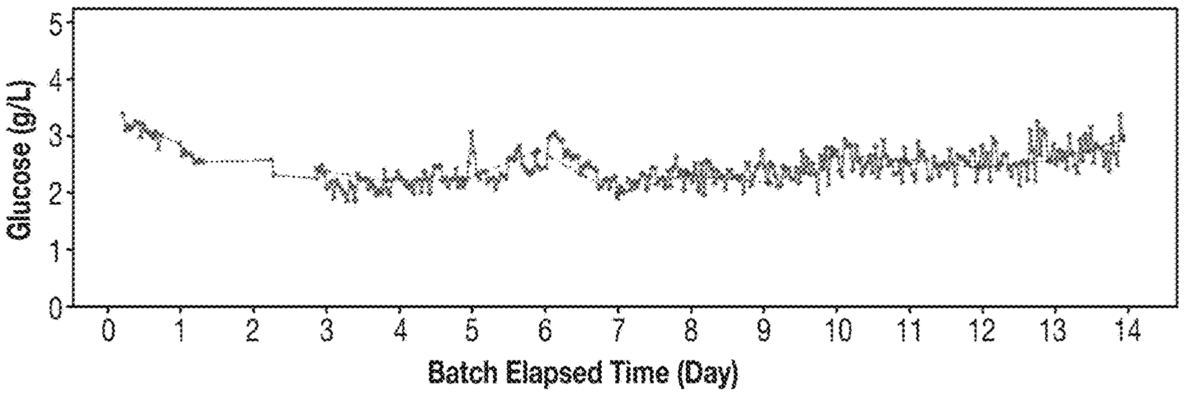

The Cell Line 2 glucose trends show similar results to that of Cell Line 1 and can be seen in FIG. 14A-FIG. 14C. The Batch D trend, FIG. 14A, shows the typical trajectory for the bolus fed process for Cell Line 2 with the expected large daily peaks of glucose from the single feed delivery. Additionally, Raman monitoring displays a much more information rich process which is more reflective of glucose trends when compared to single daily offline measurements. As Cell Line 2 has a greater demand for glucose the spread in concentration range is wider than Cell Line 1 with a process range of 0.5-4.5 g/l. The RMSEP for the glucose model in Batch D was 0.2369 g/l which was inside the acceptance criteria for performance and indicates that the data being provided by the model is accurately reflecting the actual process values. Batches E and F, FIG. 14B and FIG. 14C respectively, were controlled for 11 days to the setpoint of 2 g/l.

A key difference observed in these batches was that feed control was initiated on Day 03 whereas the manual bolus fed batch began on Day 04 when the glucose level had reduced further. Both Batch E and Batch F controlled glucose well and an RMSEP of 0.2516 g/l and 0.2119 g/l, respectively, indicates the model performance was strong in each case. It was noted that the Batch F glucose setpoint began to drift upward from the target of 2 g/l from Day 09 of the process, which was believed to be due to a calibration issue with the pump used to deliver the glucose feed. Despite this, Batch F had a tight glucose control range and only went outside acceptance criteria of +/−0.5 g/l of the target on the final day of the process.

Raman based feedback control of glucose for both Cell Line 1 and Cell Line 2 provided the bioreactor environment with a more stable supply of glucose and prevented drastic shifts in glucose concentrations as seen in the bolus fed batches. MAb bioreactor process development and optimization is focused on the production of high product titer with a well-defined and controlled product quality profile. The mechanism of feedback control presented here is repeatable and consistent and provided a well defined feed profile for both Cell Line 1 and Cell Line 2.

PAT tools, including Raman spectroscopy present themselves as a relatively low-cost inclusion to process development outside of initial investment. Large amounts of process data are gathered very quickly in the early stages of process development by execution of high-throughput and Design of Experiments bioreactor batches. Inclusion of Raman probes for data collection in early development batches such as these allows for an intense data collection and model creation phase to occur very early which will not interfere with the tight time constraints of process development (e.g. mAb process development) and will allow for implementation of advanced feedback control strategies such as those presented for Cell Line 1 and Cell Line 2. As has been shown in this study, this technology can provide a wealth of additional process information as a monitoring tool, Batch A and Batch D both identified peaks and toughs in the glucose trends which would have otherwise been unnoticed when trending single daily offline measurements. Combination of this data rich approach with process control strategies can stand to change and improve the approach taken in process development and intensification.

Evaluation of Bioreactor performance: Offline Sample Analysis and Online Parameter Trending. The objective of this study was to deploy Raman based automated feedback control on two exemplary cell line processes and assess the impact of this feedback control on each process. Both processes were considered in terms of the impact automated feedback control had on process variables associated with bioreactor health, productivity and environmental conditions. Any observed impacts are discussed in relation to the development stage of each process and how a PAT focused approach at this stage may support process development and intensification.

FIG. 15A-FIG. 15H show process trends for the bolus fed and automated feedback control batches for Cell Line 1. It can be observed that the growth and health of each bioreactor batch was comparable, as indicated by the VCD, viability and LDH trends in FIG. 15A, FIG. 15B and FIG. 15C. VCD trends for each batch peaked on day07/day08 between 8.00-8.75×10^6 cells/ml and gradually declined for the remainder of the process. Final day viability was observed between 70-75% and final day LDH was observed between 1400-1450 IU/ml for each batch. These trends and the small degree of variability observed between each batch indicated that the Raman based feedback control had no adverse impact on the Cell Line 1 process.

Figure 15A:
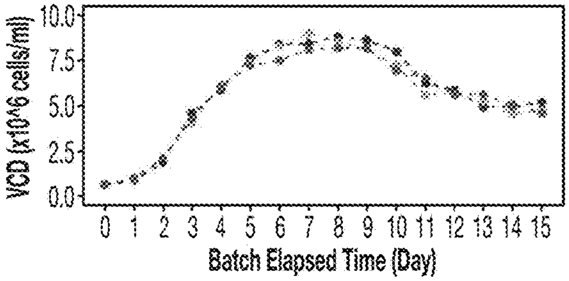
Figure 15B:
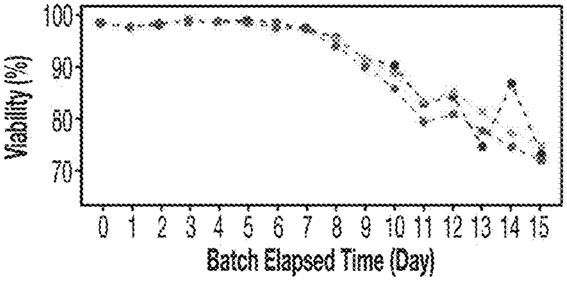
Figure 15C:
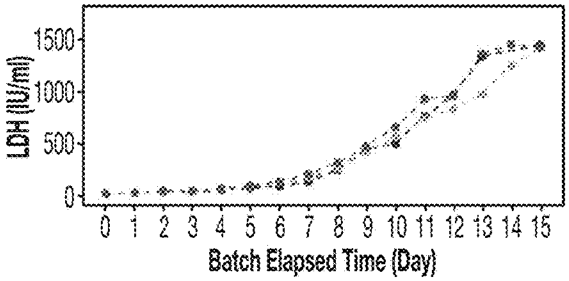
Figure 15D:
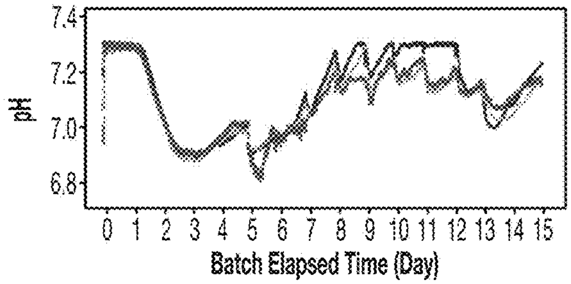
Figure 15E:
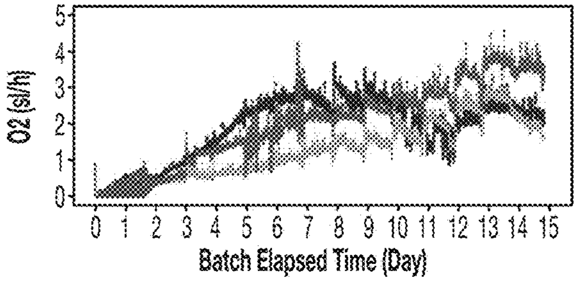

Variability in the bioreactor environment was observed depending on which feeding strategy was employed for Cell Line 1. pH trends for Batch A, B and C, FIG. 15D, were similar until day07 when bolus fed Batch A continued to increase up to pH 7.3, whereby constant CO2 addition was required to maintain pH within the setpoints for this batch from day07-day12. Raman controlled Batch B and C showed trends that differ from Batch A and maintained within the setpoint range throughout the process, particularly during day07-day12 where pH was maintained at ~pH 7.2. Online O2 trends for Batch A, B and C differ from one another as seen in FIG. 15E. Duplicate batches B and C show a gradually increasing demand for O2 to be delivered from day0-day15. The O2 demand for Batch A differs as the O2 requirement increases and decreases throughout the bioreactor process. For both O2 and pH, trends differences begin to appear on day07, this coincides with the time at which the process reaches peak VCD. The difference in these trends observed in the bolus fed Batch A vs feedback control batches B and C would potentially indicate a difference in cellular metabolism of bolus and feedback control batches after peak VCD. The gradually increasing demand in O2 observed throughout feedback control batches B and C along with pH trends which do not reach the upper control limits may indicate that the environment maintained in the feedback control batches is more favourable in terms of cellular metabolism, potentially attributed to a more consistent delivery of glucose feeds.

Figure 15F:
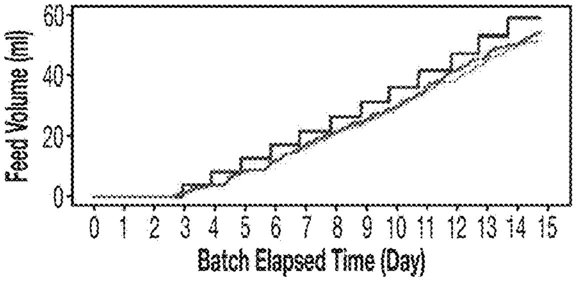

The total amount of glucose feed delivered in automated feedback control batches for Cell Line 1 was less than the bolus fed batch. FIG. 15F shows a final day glucose feed volume of 51.5 ml and 54.5 ml for Batch B and C compared to a final day glucose feed volume of 59 ml for Batch A, indicating 12.7% and 7.6% less glucose feed being delivered in Batch B and C respectively. As the feedback control batches B and C are maintaining a target concentration of 1 g/L automatically at every interval where a Raman measurement is obtained there is a greater level of control over glucose concentration in the bioreactor vs the bolus fed Batch A. Automated glucose delivery, here, is based on real time measurements which capture the demand for glucose in the bioreactor more accurately than a single daily offline sample. The bolus delivery of glucose is based on feed targets which have been established from previous batch execution and by measuring the glucose concentration offline. This approach does not take into account the current performance of the bioreactor and can potentially lead to an overestimation of the glucose requirement, as identified here in Batch A.

Figure 15G:
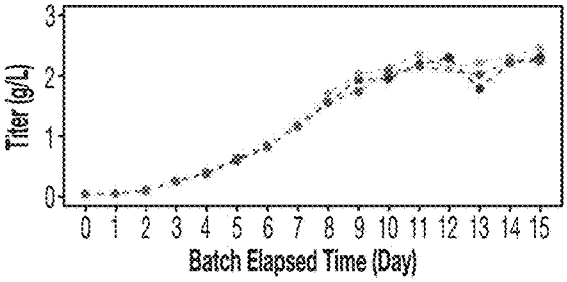
Figure 15H:
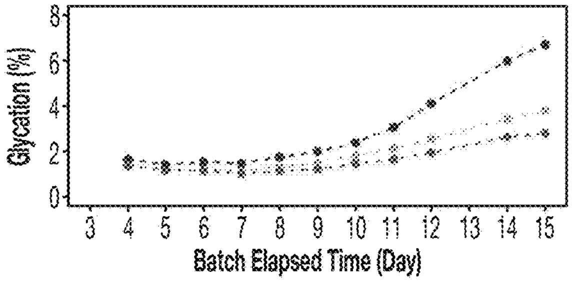

Automated feedback control for Cell Line 1 resulted in a comparable product titer when compared to the bolus feed strategy, FIG. 15G shows a final day titer between 2.2-2.5 g/L for each batch as expected. A reduction of overall product glycation in both Batch B and Batch C was observed when compared to the bolus fed Batch A. Final day glycation for Batch A was observed at 6.68% while Batch B was observed at 3.78% and Batch C at 2.81%, representing a 43.4% and 57.9% reduction in glycation respectively, as seen in FIG. 15H. A comparable final day titer in all 3 Cell Line 1 batches further serves to support that no negative impact is observed on this process when Raman based feedback control is used. What is notable is the marked improvement in product glycation, this can be attributed to the lower total glucose volume in both Batch B and C as a result of Raman based feedback control. The overall concentration of glucose in a bioreactor directly impacts the level of glycation and control of this CQA identifies a key process improvement associated with the PAT approach that could otherwise not be achieved during process development.

Figure 16A:
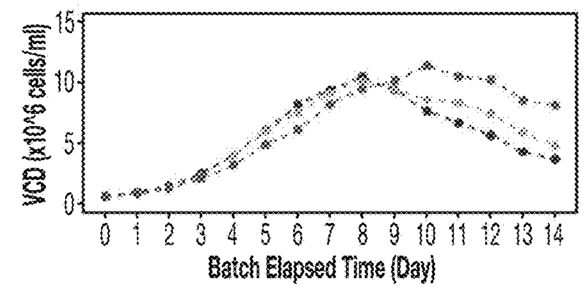
Figure 16B:
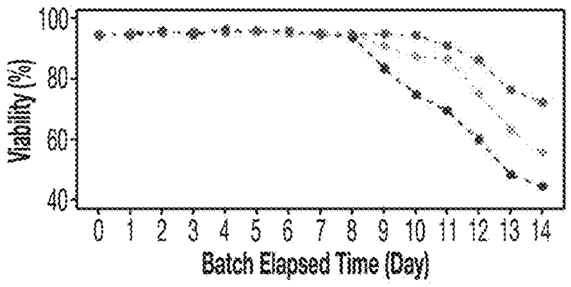
Figure 16C:
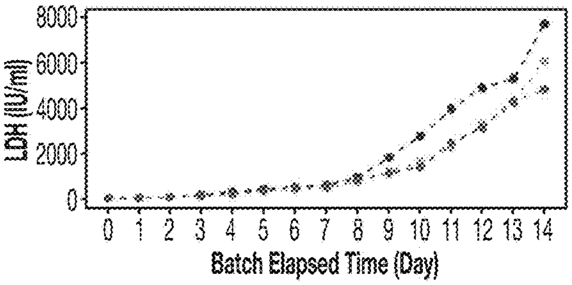

A similar assessment of process variation was considered for the bolus fed and automated feedback control batches for Cell Line 2. FIG. 16A-FIG. 16H summarize the comparison of each batch. VCD, Viability and LDH trends indicate differences in the growth profiles of Batch D, E and F. FIG. 16A shows both the bolus fed batch D and automated feedback control batch E reached peak VCD of 10-10.5×10^6 cells/ml on day08 of the process while the automated feedback control batch F peaked on day10 at 11.97×10^6 cells/ml. The drop off in VCD was lower in the automated feedback control batches E and F than in the bolus fed batch D, with a final day VCD of 4.81×10^6 cells/ml and 8.07×10^6 cells/ml in batch E and F, respectively, compared to 3.65x10^6 cells/ml in batch D. The viability and LDH trends further highlight differences in bioreactor health as seen in FIG. 16B and FIG. 16C. Bioreactor viability remained higher in both automated feedback control batches than the bolus fed batch, with batch E (56%) and F (72.5%) showing 11.1% and 27.6% greater viability than batch D (44.9%) on the final day of the process. LDH was observed to be higher in the bolus fed batch from day08 through to the day14 than the automated feedback control batches with batch E (6053 IU/ml) and F (4834.5 IU/ml) observed to be 21% and 37% lower than batch D (7694 IU/ml) on day14. A less severe drop off in both VCD and viability for Batch E and F along with a lower LDH would indicate that a Raman based feedback control strategy to a glucose setpoint of 2 g/L has a positive effect on cellular growth and health in the bioreactor. A steadier glucose concentration in the bioreactor environment appears to be much more favorable for the Cell Line 2 process than the daily peaks and troughs associated with bolus feeding as seen in Batch D. An ability to keep a process alive and generating product output for longer serves as another justification for inclusion of PAT at the process development stage as the same prolonged level of growth may not be attainable with traditional development strategies.

Figure 16D:
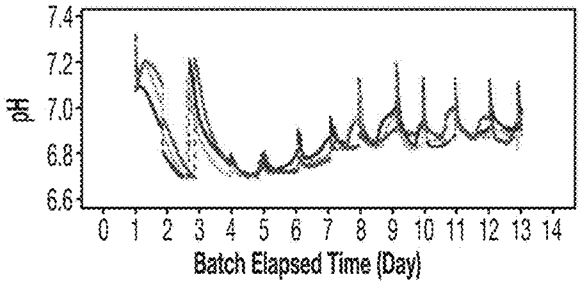
Figure 16E:
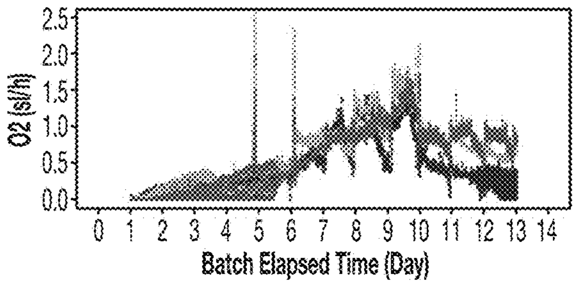
Figure 16F:
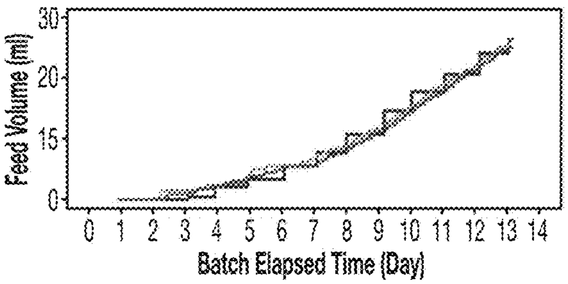

Bioreactor pH, O2 flow and glucose feed volume were tracked online up to day13 for each process, a connection issue prevented the remainder of the process data from being recorded in each case. It was observed that the pH trend for each batch was similar, FIG. 16D, showing daily spikes up to pH 7.1 which coincided with daily addition of the complex feeds. FIG. 16E shows that O2 demand was also consistent across all 3 batches, each with a gradually increasing demand for O2 up until day10. From day10 onward, the batch requirements for O2 differed as both batch E and F O2 flow maintains at >0.5 sl/h while Batch D O2 flow gradually declines to below 0.5 sl/h. FIG. 15F shows a similar final day glucose feed volume for Batch D, E and F of ~26 mls. Consistency in these parameters indicates no negative impact associated with Raman based feedback control for the Cell Line 2 process. The drop off in O2 demand in the bolus Batch D is likely due to the lower amount of viable cell in this batch from day10 onward. Interestingly the total glucose delivered in both the bolus fed Batch D and Raman based feedback control batches E and F were comparable which would indicate the previous observed impact to bioreactor health was not due to a lesser amount of feed delivery but instead the delivery system of the glucose feed, single daily bolus vs multiple smaller feeds a day.

Figure 16G:
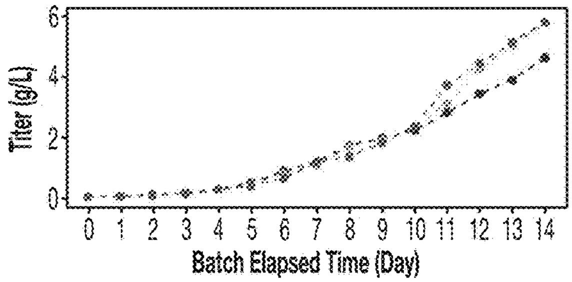
Figure 16H:
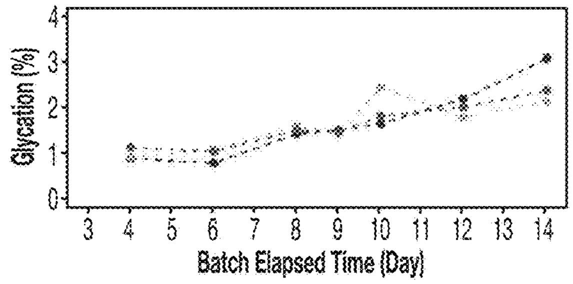

Productivity of the Cell Line 2 process was increased when automated feedback control of glucose was used. FIG. 16G shows that the final day titer for batch E (5.75 g/L) and batch F (5.77 g/L) were 25% higher than the bolus fed batch D (4.6 g/L). The quality of the product titer was also improved in the automated feedback control batches, FIG. 16H, where final day product glycation of the bolus fed batch D was observed to be 3.06% while batch E and F were observed to be lower at 2.13% and 2.37% respectively. While all three batches show a similar total volume of glucose added, the glycation results would indicate that continuous control to a setpoint concentration is a more favorable strategy in terms of product quality. The improvements in growth, product output and quality show that adoption of PAT development strategies for a more intensified process such as that of Cell Line 2 can drive development further and produce results that may be out of reach with a traditional bioreactor process.

Once daily, bolus delivery of glucose as a platform feeding strategy is widely considered in mAb bioreactor process development as it has been shown to adequately deliver nutrients to the bioreactor to facilitate growth and product output. A primary concern of this approach to nutrient delivery is the impact on product quality. Large daily swings in glucose concentration can be observed in bolus fed batches in this study, FIG. 13A and FIG. 14A. The influence of glucose on product quality is seen primarily in its promotion of product glycation. Glycation is a critical quality attribute of mAb bioreactor processes, the direct impact of glycation on mAbs is varied and its impact is most likely dependent on the mAb sites which are glycated and the overall amount of glycation present.

Automation of this process removes the extra resource requirements of a more frequent bioreactor feeding schedule and adds a QbD consideration to process development which can allow for further improvements to be made, using techniques that complement current development methods. The automated feedback control to a setpoint glucose concentration using a Raman based PLS model as shown in this study had a direct positive influence on each cell line process without any additional resource requirements. Automated feedback control for Cell Line 1 resulted in a reduction of overall product glycation in both Batch B and Batch C when compared to the bolus fed Batch A, while maintaining a comparable growth profile and product output. This improvement can be attributed to the consistent delivery and overall reduced volume of glucose feed required for the automated feedback control batches B and C. Cell Line 1 is representative of a platform process in late stage development. While significant process development has been completed for this cell line, introduction of PAT tools such as Raman based automated feedback control could stand to benefit process development without any expected negative impact on the process designed up to this point.

Cell Line 2 is representative of a more intensified process in an earlier stage of development than Cell Line 1. Process intensification in mAb producing bioreactors is mainly dependent on the biological limit of the process. Media formulation and enrichment as well as feeding strategy optimization are important to maintain higher VCD, cellular metabolism and productivity of intensified processes. The automation of glucose feeding for Cell Line 2 allowed for a more optimized feeding strategy to be tested. While total volume of glucose delivered was similar in both bolus and automated feedback control batches, a number of process improvements were observed. An improved growth and viability profile coupled with a greater product output and an improved product quality in both automated feedback control batches for Cell Line 2 highlights how effective PAT tools can be in the development process. The ability to directly influence product quality and output in process development is aligned with the goals of the QbD initiative.

Implementation of PAT technology such as Raman spectroscopy at early or late stage development can have a significant impact on process development, scale up and the robustness of manufacturing processes. Here, two CHO cell line bioreactor processes saw an indication of improvement in the efficiency of their current process when employing PAT methods at the development stage.

Employment of methods such as automated feedback control with Raman in the development phase is able to generate valuable data, and there is low risk involved. The ability to standardize PAT in process development is able to lead to a more efficient and cost-effective manufacturing process. Increased product output and/or improved product quality at manufacturing scale, as a direct result of more efficient development, may influence the dosage requirements for a patient (which could lead to more doses of a product generated per batch resulting in major cost and time savings. The consideration of technology such as this at development and implementation in commercial manufacturing creates an end to end QbD approach which will maximize process efficiency and meet the demands for novel mAb therapies.

The results provided here demonstrated inclusion of Raman spectroscopy as a PAT tool in process development can improve product output and reduce overall product glycation. For example, the Cell Line 1 process was improved by reducing total glucose delivery to the bioreactor and in turn reducing the overall product glycation by 43.7% and 57.9% in the Raman based feedback control batches while maintaining comparable growth profiles and product output. In addition, the Cell Line 2 process was also improved with a prolonged cellular health and greatly reduced drop off in cellular viability as the process progressed. This improvement had a knock-on effect of increasing product output for this process by up to 25%. Thus, inclusion of Raman spectroscopy as a PAT tool in process development can have a significant impact on process development, scale up and the robustness of manufacturing processes.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed is:

1. A method of producing a glycosylated molecule having a desired glycan structure, the method comprising:
- measuring one or more glycan structures using a process analytical technology (PAT) tool to result in spectral data, wherein the measuring is within a bioreactor having a volume of equal to or above 1,000 liters;
- determining, by at least one computing device using one or more regression models and based on the measured spectral data, a level of the one or more glycan structures within the bioreactor, wherein the one or more regression models are generated using trial runs from at least one bioreactor having a volume less than or equal to 50 liters and at least one bioreactor having a volume equal to or above 1,000 liters; and
- maintaining one or more operating parameters of the bioreactor when:
  - the level of a desired glycan structure is above a pre-defined threshold, or
  - the level of an undesired glycan structure is below a pre-defined threshold; and selectively modifying one or more operating parameters of the bioreactor when:
    - the level of a desired glycan structures is below a pre-defined threshold, or
    - the level of an undesired glycan structure is above a pre-defined threshold.

2. The method of claim 1, wherein measuring is performed in-line, at-line, on-line, off-line, or a combination thereof.

3. The method of claim 1, wherein measuring occurs:
(a) more than once daily;
(b) about every 5 to 60 minutes;
(c) about every 10 to 30 minutes;
(d) about every 10 to 20 minutes; or
(e) about every 12.5 minutes.

4. The method of claim 1, wherein measuring is within a bioreactor having a volume of:
(a) about 2,000 liters or more;
(b) about 5,000 liters or more;
(c) about 10,000 liters or more;
(d) about 15,000 liters or more;
(e) about 10,000 liters to about 25,000 liters; or
(f) about 15,000 liters.

5. The method of claim 1, wherein the determining step is performed on-site or off-site.

6. The method of claim 1, wherein the desired glycan structure is selected from the group consisting of: G0F-GlcNac, G0, G0F, G1F, and G2F, or a combination thereof.

7. The method of claim 1, wherein the bioreactor is a batch reactor, a fed-batch reactor, a perfusion reactor, or a combination thereof.

8. The method of claim 1, wherein the one or more operating parameters comprise a pH level, a nutrient level, a culture media concentration, a frequency interval for culture media addition, or a combination thereof,
- wherein the nutrient level is optionally selected from the group consisting of: a concentration of glucose, a concentration of lactate, a concentration of glutamine, and a concentration of ammonium ions; and
- wherein the concentration of glucose is optionally automatically modified based on the measured spectral data.

9. The method of claim 1, wherein the PAT tool utilizes or otherwise comprises Raman spectroscopy.

10. The method of claim 1, wherein the one or more regression models comprise a partial least squares (PLS) model.

* * * * *